United States Patent
Perkins et al.

(10) Patent No.: US 10,286,215 B2
(45) Date of Patent: May 14, 2019

(54) OPTICALLY COUPLED COCHLEAR IMPLANT SYSTEMS AND METHODS

(75) Inventors: Rodney C. Perkins, Woodside, CA (US); Sunil Puria, Sunnyvale, CA (US); Paul C. Rucker, San Francisco, CA (US)

(73) Assignee: EarLens Corporation, Menlo Park, CA (US)

( * ) Notice: Subject to any disclaimer, the term of this patent is extended or adjusted under 35 U.S.C. 154(b) by 0 days.

(21) Appl. No.: 12/818,434

(22) Filed: Jun. 18, 2010

(65) Prior Publication Data

US 2011/0144719 A1   Jun. 16, 2011

Related U.S. Application Data

(60) Provisional application No. 61/220,124, filed on Jun. 24, 2009, provisional application No. 61/218,377, filed on Jun. 18, 2009.

(51) Int. Cl.
   *A61N 1/00* (2006.01)
   *A61N 1/372* (2006.01)
   (Continued)

(52) U.S. Cl.
   CPC ..... *A61N 1/37217* (2013.01); *A61N 1/36036* (2017.08); *H04B 10/1141* (2013.01); *A61N 1/0541* (2013.01); *H04R 25/606* (2013.01)

(58) Field of Classification Search
   CPC .............. H04R 25/606; A61N 1/37217; A61N 1/36036; A61N 1/0541; H04B 10/141
   (Continued)

(56) References Cited

U.S. PATENT DOCUMENTS

| 3,209,082 A | 9/1965 | McCarrell et al. |
|---|---|---|
| 3,440,314 A | 4/1969 | Frisch |

(Continued)

FOREIGN PATENT DOCUMENTS

| CN | 1176731 A | 3/1998 |
|---|---|---|
| CN | 101459868 A | 6/2009 |

(Continued)

OTHER PUBLICATIONS

Atasoy [Paper] "Opto-acoustic Imaging" for BYM504E Biomedical Imaging Systems class at ITU, downloaded from the Internet <<http://www2.itu.edu.tr/~cilesiz/courses/BYM504-2005-OA_504041413.pdf>>, 14 pages, presented May 13, 2005.

(Continued)

*Primary Examiner* — Mallika D Fairchild
(74) *Attorney, Agent, or Firm* — Wilson Sonsini Goodrich and Rosati, P.C.

(57) ABSTRACT

An output assembly is sized for placement in the middle and inner ear, such that removal of bone can be decreased. The output assembly may comprise at least one photo detector, a demultiplexer and an electrode array sized to pass through an incision in the eardrum. An input transducer assembly is configured to transmit a multiplexed optical signal to the output assembly. The input assembly can be configured to transmit the multiplexed optical signal through the eardrum, such that tissue removal can be decreased and the device can be placed without removal of bone, for example. The multiplexed optical signal may comprise a pulse width modulated signal so as to decrease the effect of non-linearities of the light source and light detector and provide quality sound to the user.

40 Claims, 12 Drawing Sheets

(51) Int. Cl.
  *H04B 10/114* (2013.01)
  *A61N 1/36* (2006.01)
  *A61N 1/05* (2006.01)
  *H04R 25/00* (2006.01)

(58) Field of Classification Search
  USPC .......................................... 607/137, 55–57
  See application file for complete search history.

(56) References Cited

U.S. PATENT DOCUMENTS

| | | |
|---|---|---|
| 3,449,768 A | 6/1969 | James |
| 3,549,818 A | 12/1970 | Turner et al. |
| 3,585,416 A | 6/1971 | Mellen |
| 3,594,514 A | 7/1971 | Wingrove |
| 3,710,399 A | 1/1973 | Hurst |
| 3,712,962 A | 1/1973 | Epley |
| 3,764,748 A | 10/1973 | Branch et al. |
| 3,808,179 A | 4/1974 | Gaylord |
| 3,870,832 A | 3/1975 | Fredrickson |
| 3,882,285 A | 5/1975 | Nunley et al. |
| 3,985,977 A | 10/1976 | Beaty et al. |
| 4,002,897 A | 1/1977 | Kleinman et al. |
| 4,061,972 A | 12/1977 | Burgess |
| 4,075,042 A | 2/1978 | Das |
| 4,098,277 A | 7/1978 | Mendell |
| 4,109,116 A | 8/1978 | Victoreen |
| 4,120,570 A | 10/1978 | Gaylord |
| 4,207,441 A | 6/1980 | Chouard et al. |
| 4,248,899 A | 2/1981 | Lyon et al. |
| 4,252,440 A | 2/1981 | Frosch et al. |
| 4,281,419 A | 8/1981 | Treace |
| 4,303,772 A | 12/1981 | Novicky |
| 4,319,359 A | 3/1982 | Wolf |
| 4,334,315 A | 6/1982 | Ono et al. |
| 4,334,321 A | 6/1982 | Edelman |
| 4,339,954 A | 7/1982 | Anson et al. |
| 4,357,497 A | 11/1982 | Hochmair et al. |
| 4,380,689 A | 4/1983 | Giannetti |
| 4,428,377 A | 1/1984 | Zollner et al. |
| 4,524,294 A | 6/1985 | Brody |
| 4,540,761 A | 9/1985 | Kawamura et al. |
| 4,556,122 A | 12/1985 | Goode |
| 4,592,087 A | 5/1986 | Killion |
| 4,606,329 A | 8/1986 | Hough |
| 4,611,598 A | 9/1986 | Hortmann et al. |
| 4,628,907 A | 12/1986 | Epley |
| 4,641,377 A | 2/1987 | Rush et al. |
| 4,654,554 A | 3/1987 | Kishi |
| 4,689,819 A | 8/1987 | Killion |
| 4,696,287 A | 9/1987 | Hortmann et al. |
| 4,729,366 A | 3/1988 | Schaefer |
| 4,741,339 A | 5/1988 | Harrison et al. |
| 4,742,499 A | 5/1988 | Butler |
| 4,756,312 A | 7/1988 | Epley |
| 4,766,607 A | 8/1988 | Feldman |
| 4,774,933 A | 10/1988 | Hough et al. |
| 4,776,322 A | 10/1988 | Hough et al. |
| 4,782,818 A | 11/1988 | Mori |
| 4,800,884 A | 1/1989 | Heide et al. |
| 4,800,982 A | 1/1989 | Carlson |
| 4,817,607 A | 4/1989 | Tatge |
| 4,840,178 A | 6/1989 | Heide et al. |
| 4,845,755 A | 7/1989 | Busch et al. |
| 4,865,035 A | 9/1989 | Mori |
| 4,918,745 A | 4/1990 | Hutchison |
| 4,932,405 A | 6/1990 | Peeters et al. |
| 4,936,305 A | 6/1990 | Ashtiani et al. |
| 4,944,301 A | 7/1990 | Widin et al. |
| 4,948,855 A | 8/1990 | Novicky |
| 4,957,478 A | 9/1990 | Maniglia |
| 4,982,434 A | 1/1991 | Lenhardt et al. |
| 4,999,819 A | 3/1991 | Newnham et al. |
| 5,003,608 A | 3/1991 | Carlson |
| 5,012,520 A | 4/1991 | Steeger |
| 5,015,224 A | 5/1991 | Mariglia |
| 5,015,225 A | 5/1991 | Hough et al. |
| 5,031,219 A | 7/1991 | Ward et al. |
| 5,061,282 A | 10/1991 | Jacobs |
| 5,066,091 A | 11/1991 | Stoy et al. |
| 5,094,108 A | 3/1992 | Kim et al. |
| 5,117,461 A | 5/1992 | Moseley |
| 5,142,186 A | 8/1992 | Cross et al. |
| 5,163,957 A | 11/1992 | Sade et al. |
| 5,167,235 A | 12/1992 | Seacord et al. |
| 5,201,007 A | 4/1993 | Ward et al. |
| 5,259,032 A | 11/1993 | Perkins et al. |
| 5,272,757 A | 12/1993 | Scofield et al. |
| 5,276,910 A | 1/1994 | Buchele |
| 5,277,694 A | 1/1994 | Leysieffer et al. |
| 5,338,287 A | 8/1994 | Miller et al. |
| 5,360,388 A | 11/1994 | Spindel et al. |
| 5,378,933 A | 1/1995 | Pfannenmueller et al. |
| 5,402,496 A | 3/1995 | Soli et al. |
| 5,411,467 A | 5/1995 | Hortmann et al. |
| 5,425,104 A | 6/1995 | Shennib |
| 5,440,082 A | 8/1995 | Claes |
| 5,440,237 A | 8/1995 | Brown et al. |
| 5,455,994 A | 10/1995 | Termeer et al. |
| 5,456,654 A | 10/1995 | Ball |
| 5,531,787 A * | 7/1996 | Lesinski et al. ............... 623/10 |
| 5,531,954 A | 7/1996 | Heide et al. |
| 5,535,282 A | 7/1996 | Luca |
| 5,554,096 A | 9/1996 | Ball |
| 5,558,618 A | 9/1996 | Maniglia |
| 5,571,148 A * | 11/1996 | Loeb et al. ..................... 607/57 |
| 5,572,594 A | 11/1996 | Devoe et al. |
| 5,606,621 A | 2/1997 | Reiter et al. |
| 5,624,376 A | 4/1997 | Ball et al. |
| 5,707,338 A | 1/1998 | Adams et al. |
| 5,715,321 A | 2/1998 | Andrea et al. |
| 5,721,783 A | 2/1998 | Anderson |
| 5,722,411 A | 3/1998 | Suzuki et al. |
| 5,729,077 A | 3/1998 | Newnham et al. |
| 5,740,258 A | 4/1998 | Goodwin-Johansson |
| 5,749,912 A | 5/1998 | Zhang et al. |
| 5,762,583 A | 6/1998 | Adams et al. |
| 5,772,575 A | 6/1998 | Lesinski et al. |
| 5,774,259 A | 6/1998 | Saitoh et al. |
| 5,782,744 A | 7/1998 | Money |
| 5,788,711 A | 8/1998 | Lehner et al. |
| 5,795,287 A | 8/1998 | Ball et al. |
| 5,797,834 A | 8/1998 | Goode |
| 5,800,336 A | 9/1998 | Ball et al. |
| 5,804,109 A | 9/1998 | Perkins |
| 5,804,907 A | 9/1998 | Park et al. |
| 5,814,095 A | 9/1998 | Muller et al. |
| 5,824,022 A * | 10/1998 | Zilberman et al. ............. 607/57 |
| 5,825,122 A | 10/1998 | Givargizov et al. |
| 5,836,863 A | 11/1998 | Bushek et al. |
| 5,842,967 A | 12/1998 | Kroll |
| 5,851,199 A | 12/1998 | Peerless et al. |
| 5,857,958 A | 1/1999 | Ball et al. |
| 5,859,916 A | 1/1999 | Ball et al. |
| 5,879,283 A | 3/1999 | Adams et al. |
| 5,888,187 A | 3/1999 | Jaeger et al. |
| 5,897,486 A | 4/1999 | Ball et al. |
| 5,899,847 A | 5/1999 | Adams et al. |
| 5,900,274 A | 5/1999 | Chatterjee et al. |
| 5,906,635 A | 5/1999 | Maniglia |
| 5,913,815 A | 6/1999 | Ball et al. |
| 5,922,077 A | 7/1999 | Espy et al. |
| 5,935,170 A | 8/1999 | Haakansson et al. |
| 5,940,519 A | 8/1999 | Kuo |
| 5,949,895 A | 9/1999 | Ball et al. |
| 5,984,859 A | 11/1999 | Lesinski |
| 5,987,146 A | 11/1999 | Pluvinage et al. |
| 6,001,129 A | 12/1999 | Bushek et al. |
| 6,005,955 A | 12/1999 | Kroll et al. |
| 6,024,717 A | 2/2000 | Ball et al. |
| 6,038,480 A | 3/2000 | Hrdlicka et al. |
| 6,045,528 A | 4/2000 | Arenberg et al. |
| 6,050,933 A | 4/2000 | Bushek et al. |
| 6,068,589 A | 5/2000 | Neukermans |

(56) References Cited

U.S. PATENT DOCUMENTS

| | | |
|---|---|---|
| 6,068,590 A | 5/2000 | Brisken |
| 6,084,975 A | 7/2000 | Perkins et al. |
| 6,093,144 A | 7/2000 | Jaeger et al. |
| 6,137,889 A | 10/2000 | Shennib et al. |
| 6,139,488 A | 10/2000 | Ball |
| 6,153,966 A | 11/2000 | Neukermans |
| 6,174,278 B1 | 1/2001 | Jaeger et al. |
| 6,181,801 B1 | 1/2001 | Puthuff et al. |
| 6,190,305 B1 | 2/2001 | Ball et al. |
| 6,190,306 B1 | 2/2001 | Kennedy |
| 6,208,445 B1 | 3/2001 | Reime |
| 6,216,040 B1 | 4/2001 | Harrison |
| 6,217,508 B1 | 4/2001 | Ball et al. |
| 6,222,302 B1 | 4/2001 | Imada et al. |
| 6,222,927 B1 | 4/2001 | Feng et al. |
| 6,240,192 B1 | 5/2001 | Brennan et al. |
| 6,241,767 B1 | 6/2001 | Stennert et al. |
| 6,261,224 B1 | 7/2001 | Adams et al. |
| 6,277,148 B1 | 8/2001 | Dormer |
| 6,312,959 B1 | 11/2001 | Datskos |
| 6,339,648 B1 | 1/2002 | McIntosh et al. |
| 6,342,035 B1 | 1/2002 | Kroll et al. |
| 6,354,990 B1 | 3/2002 | Juneau et al. |
| 6,366,863 B1 | 4/2002 | Bye et al. |
| 6,374,143 B1 | 4/2002 | Berrang et al. |
| 6,385,363 B1 | 5/2002 | Rajic et al. |
| 6,387,039 B1 | 5/2002 | Moses |
| 6,390,971 B1 * | 5/2002 | Adams et al. ............ 600/25 |
| 6,393,130 B1 | 5/2002 | Stonikas et al. |
| 6,422,991 B1 | 7/2002 | Jaeger |
| 6,432,248 B1 | 8/2002 | Popp et al. |
| 6,436,028 B1 | 8/2002 | Dormer |
| 6,438,244 B1 | 8/2002 | Juneau et al. |
| 6,445,799 B1 | 9/2002 | Taenzer et al. |
| 6,473,512 B1 | 10/2002 | Juneau et al. |
| 6,475,134 B1 | 11/2002 | Ball et al. |
| 6,491,622 B1 | 12/2002 | Kasic, II et al. |
| 6,491,644 B1 | 12/2002 | Vujanic et al. |
| 6,491,722 B1 | 12/2002 | Kroll et al. |
| 6,493,453 B1 | 12/2002 | Glendon |
| 6,493,454 B1 | 12/2002 | Loi et al. |
| 6,498,858 B2 | 12/2002 | Kates |
| 6,507,758 B1 * | 1/2003 | Greenberg et al. ............ 607/54 |
| 6,519,376 B2 | 2/2003 | Biagi et al. |
| 6,536,530 B2 | 3/2003 | Schultz et al. |
| 6,537,200 B2 | 3/2003 | Leysieffer et al. |
| 6,547,715 B1 | 4/2003 | Mueller et al. |
| 6,549,633 B1 | 4/2003 | Westermann |
| 6,554,761 B1 | 4/2003 | Puria et al. |
| 6,575,894 B2 | 6/2003 | Leysieffer et al. |
| 6,592,513 B1 | 7/2003 | Kroll et al. |
| 6,603,860 B1 | 8/2003 | Taezner et al. |
| 6,620,110 B2 | 9/2003 | Schmid |
| 6,626,822 B1 | 9/2003 | Jaeger et al. |
| 6,629,922 B1 | 10/2003 | Puria et al. |
| 6,643,378 B2 | 11/2003 | Schumaier |
| 6,668,062 B1 | 12/2003 | Luo et al. |
| 6,676,592 B2 | 1/2004 | Ball et al. |
| 6,695,943 B2 | 2/2004 | Juneau et al. |
| 6,724,902 B1 | 4/2004 | Shennib et al. |
| 6,728,024 B2 | 4/2004 | Ribak |
| 6,735,318 B2 | 5/2004 | Cho |
| 6,754,358 B1 | 6/2004 | Boeson et al. |
| 6,754,537 B1 | 6/2004 | Harrison et al. |
| 6,801,629 B2 | 10/2004 | Brimhall et al. |
| 6,829,363 B2 | 12/2004 | Sacha |
| 6,842,647 B1 | 1/2005 | Griffith et al. |
| 6,888,949 B1 | 5/2005 | Vanden Berghe et al. |
| 6,900,926 B2 | 5/2005 | Ribak |
| 6,912,289 B2 | 6/2005 | Vonlanthen et al. |
| 6,920,340 B2 | 7/2005 | Laderman |
| 6,931,231 B1 | 8/2005 | Griffin |
| 6,940,989 B1 | 9/2005 | Shennib et al. |
| D512,979 S | 12/2005 | Corcoran et al. |
| 6,975,402 B2 | 12/2005 | Bisson et al. |
| 6,978,159 B2 | 12/2005 | Feng et al. |
| 7,024,010 B2 | 4/2006 | Saunders et al. |
| 7,043,037 B2 | 5/2006 | Lichtblau |
| 7,050,675 B2 | 5/2006 | Zhou |
| 7,057,256 B2 | 6/2006 | Carey, III et al. |
| 7,058,182 B2 | 6/2006 | Kates |
| 7,072,475 B1 | 7/2006 | DeNap et al. |
| 7,076,076 B2 | 7/2006 | Bauman |
| 7,095,981 B1 | 8/2006 | Voroba et al. |
| 7,167,572 B1 | 1/2007 | Harrison et al. |
| 7,174,026 B2 | 2/2007 | Niederdrank |
| 7,179,238 B2 | 2/2007 | Hissong |
| 7,203,331 B2 | 4/2007 | Boesen |
| 7,239,069 B2 | 7/2007 | Cho |
| 7,245,732 B2 | 7/2007 | Jorgensen et al. |
| 7,255,457 B2 | 8/2007 | Ducharme et al. |
| 7,289,639 B2 | 10/2007 | Abel et al. |
| 7,322,930 B2 | 1/2008 | Jaeger et al. |
| 7,349,741 B2 | 3/2008 | Maltan et al. |
| 7,354,792 B2 | 4/2008 | Carey, III et al. |
| 7,376,563 B2 | 5/2008 | Leysieffer et al. |
| 7,390,689 B2 | 6/2008 | Mazur et al. |
| 7,394,909 B1 | 7/2008 | Widmer et al. |
| 7,421,087 B2 | 9/2008 | Perkins et al. |
| 7,424,122 B2 | 9/2008 | Ryan |
| 7,444,877 B2 | 11/2008 | Li et al. |
| 7,547,275 B2 | 6/2009 | Cho |
| 7,630,646 B2 | 12/2009 | Anderson et al. |
| 7,645,877 B2 | 1/2010 | Gmeiner et al. |
| 7,668,325 B2 | 2/2010 | Puria et al. |
| 7,867,160 B2 | 1/2011 | Pluvinage et al. |
| 7,883,535 B2 | 2/2011 | Cantin et al. |
| 7,983,435 B2 | 7/2011 | Moses |
| 8,116,494 B2 | 2/2012 | Rass |
| 8,157,730 B2 | 4/2012 | Leboeuf et al. |
| 8,204,786 B2 | 6/2012 | Leboeuf et al. |
| 8,251,903 B2 | 8/2012 | Leboeuf et al. |
| 8,320,982 B2 | 11/2012 | Leboeuf et al. |
| 8,401,214 B2 | 3/2013 | Perkins et al. |
| 8,512,242 B2 | 8/2013 | Leboeuf et al. |
| 8,545,383 B2 | 10/2013 | Wenzel et al. |
| 8,600,089 B2 | 12/2013 | Wenzel et al. |
| 8,647,270 B2 | 2/2014 | Leboeuf et al. |
| 8,652,040 B2 | 2/2014 | Leboeuf et al. |
| 8,700,111 B2 | 4/2014 | Leboeuf et al. |
| 8,702,607 B2 | 4/2014 | Leboeuf et al. |
| 8,715,153 B2 | 5/2014 | Puria et al. |
| 8,715,154 B2 | 5/2014 | Perkins et al. |
| 8,787,609 B2 | 7/2014 | Perkins et al. |
| 8,788,002 B2 | 7/2014 | Leboeuf et al. |
| 8,845,705 B2 | 9/2014 | Perkins et al. |
| 8,885,860 B2 | 11/2014 | Djalilian et al. |
| 8,886,269 B2 | 11/2014 | Leboeuf et al. |
| 8,888,701 B2 | 11/2014 | Leboeuf et al. |
| 8,923,941 B2 | 12/2014 | Leboeuf et al. |
| 8,929,965 B2 | 1/2015 | Leboeuf et al. |
| 8,929,966 B2 | 1/2015 | Leboeuf et al. |
| 8,934,952 B2 | 1/2015 | Leboeuf et al. |
| 8,942,776 B2 | 1/2015 | Leboeuf et al. |
| 8,961,415 B2 | 2/2015 | Leboeuf et al. |
| 8,986,187 B2 | 3/2015 | Perkins et al. |
| 8,989,830 B2 | 3/2015 | Leboeuf et al. |
| 9,044,180 B2 | 6/2015 | Leboeuf et al. |
| 9,055,379 B2 | 6/2015 | Puria et al. |
| 9,131,312 B2 | 9/2015 | Leboeuf et al. |
| 9,277,335 B2 | 3/2016 | Perkins et al. |
| 9,289,135 B2 | 3/2016 | Leboeuf et al. |
| 9,289,175 B2 | 3/2016 | Leboeuf et al. |
| 9,301,696 B2 | 4/2016 | Leboeuf et al. |
| 9,314,167 B2 | 4/2016 | Leboeuf et al. |
| 9,392,377 B2 | 7/2016 | Olsen et al. |
| 9,427,191 B2 | 8/2016 | Leboeuf et al. |
| 9,521,962 B2 | 12/2016 | Leboeuf |
| 9,538,921 B2 | 1/2017 | Leboeuf et al. |
| 9,750,462 B2 | 9/2017 | Leboeuf et al. |
| 9,788,785 B2 | 10/2017 | Leboeuf |
| 9,788,794 B2 | 10/2017 | Leboeuf et al. |
| 9,794,653 B2 | 10/2017 | Aumer et al. |
| 9,801,552 B2 | 10/2017 | Romesburg et al. |

(56) References Cited

U.S. PATENT DOCUMENTS

| | | |
|---|---|---|
| 9,808,204 B2 | 11/2017 | Leboeuf et al. |
| 2001/0003788 A1 | 6/2001 | Ball et al. |
| 2001/0027342 A1 | 10/2001 | Dormer |
| 2001/0029313 A1 | 10/2001 | Kennedy |
| 2001/0043708 A1 | 11/2001 | Brimhall |
| 2001/0053871 A1 | 12/2001 | Zilberman et al. |
| 2001/0055405 A1 | 12/2001 | Cho |
| 2002/0012438 A1 | 1/2002 | Leysieffer et al. |
| 2002/0029070 A1* | 3/2002 | Leysieffer et al. ............ 607/57 |
| 2002/0030871 A1 | 3/2002 | Anderson et al. |
| 2002/0035309 A1 | 3/2002 | Leysieffer |
| 2002/0086715 A1 | 7/2002 | Sahagen |
| 2002/0172350 A1 | 11/2002 | Edwards et al. |
| 2002/0183587 A1 | 12/2002 | Dormer |
| 2003/0064746 A1 | 4/2003 | Rader et al. |
| 2003/0097178 A1 | 5/2003 | Roberson et al. |
| 2003/0125602 A1 | 7/2003 | Sokolich et al. |
| 2003/0142841 A1 | 7/2003 | Wiegand |
| 2003/0208099 A1 | 11/2003 | Ball |
| 2003/0220536 A1 | 11/2003 | Hissong |
| 2004/0158157 A1 | 8/2004 | Jensen et al. |
| 2004/0165742 A1 | 8/2004 | Shennib et al. |
| 2004/0184732 A1 | 9/2004 | Zhou |
| 2004/0208333 A1 | 10/2004 | Cheung et al. |
| 2004/0234089 A1 | 11/2004 | Rembrand et al. |
| 2004/0234092 A1 | 11/2004 | Wada et al. |
| 2004/0240691 A1 | 12/2004 | Grafenberg |
| 2005/0020873 A1 | 1/2005 | Berrang et al. |
| 2005/0036639 A1 | 2/2005 | Bachler et al. |
| 2005/0111683 A1 | 5/2005 | Chabries et al. |
| 2005/0163333 A1* | 7/2005 | Abel et al. ................... 381/315 |
| 2005/0226446 A1 | 10/2005 | Luo et al. |
| 2005/0267549 A1 | 12/2005 | Della Santina et al. |
| 2006/0023908 A1 | 2/2006 | Perkins et al. |
| 2006/0058573 A1 | 3/2006 | Neisz et al. |
| 2006/0062420 A1 | 3/2006 | Araki |
| 2006/0107744 A1 | 5/2006 | Li et al. |
| 2006/0129210 A1 | 6/2006 | Cantin et al. |
| 2006/0161227 A1 | 7/2006 | Walsh et al. |
| 2006/0161255 A1 | 7/2006 | Zarowski et al. |
| 2006/0177079 A1 | 8/2006 | Baekgaard Jensen et al. |
| 2006/0183965 A1 | 8/2006 | Kasic, II et al. |
| 2006/0189841 A1 | 8/2006 | Pluvinage |
| 2006/0231914 A1 | 10/2006 | Carey, III et al. |
| 2006/0233398 A1 | 10/2006 | Husung |
| 2006/0251278 A1 | 11/2006 | Puria et al. |
| 2006/0278245 A1 | 12/2006 | Gan |
| 2007/0083078 A1 | 4/2007 | Easter et al. |
| 2007/0100197 A1 | 5/2007 | Perkins et al. |
| 2007/0127748 A1 | 6/2007 | Carlile et al. |
| 2007/0135870 A1 | 6/2007 | Shanks et al. |
| 2007/0161848 A1 | 7/2007 | Dalton et al. |
| 2007/0191673 A1 | 8/2007 | Ball et al. |
| 2007/0225776 A1 | 9/2007 | Fritsch et al. |
| 2007/0236704 A1 | 10/2007 | Carr |
| 2007/0250119 A1 | 10/2007 | Tyler et al. |
| 2007/0251082 A1 | 11/2007 | Milojevic et al. |
| 2007/0286429 A1 | 12/2007 | Grafenberg et al. |
| 2008/0021518 A1 | 1/2008 | Hochmair et al. |
| 2008/0051623 A1 | 2/2008 | Schneider et al. |
| 2008/0077198 A1 | 3/2008 | Webb et al. |
| 2008/0107292 A1 | 5/2008 | Kornagel |
| 2008/0188707 A1 | 8/2008 | Bernard et al. |
| 2008/0298600 A1 | 12/2008 | Poe et al. |
| 2009/0023976 A1 | 1/2009 | Cho et al. |
| 2009/0043149 A1 | 2/2009 | Abel et al. |
| 2009/0092271 A1 | 4/2009 | Fay et al. |
| 2009/0097681 A1 | 4/2009 | Puria et al. |
| 2009/0131742 A1 | 5/2009 | Cho et al. |
| 2009/0141919 A1 | 6/2009 | Spitaels et al. |
| 2009/0157143 A1 | 6/2009 | Edler et al. |
| 2010/0034409 A1 | 2/2010 | Fay et al. |
| 2010/0048982 A1 | 2/2010 | Puria et al. |
| 2010/0114190 A1 | 5/2010 | Bendett et al. |
| 2010/0145135 A1 | 6/2010 | Ball et al. |
| 2010/0272299 A1 | 10/2010 | Van Schuylenbergh et al. |
| 2010/0312040 A1 | 12/2010 | Puria et al. |
| 2010/0317914 A1 | 12/2010 | Puria et al. |
| 2011/0125222 A1 | 5/2011 | Perkins et al. |
| 2011/0142274 A1 | 6/2011 | Perkins et al. |
| 2011/0152601 A1 | 6/2011 | Puria et al. |
| 2011/0152602 A1 | 6/2011 | Perkins et al. |
| 2011/0152603 A1 | 6/2011 | Perkins et al. |
| 2011/0152976 A1 | 6/2011 | Perkins et al. |
| 2013/0315428 A1 | 11/2013 | Perkins et al. |
| 2014/0275734 A1 | 9/2014 | Perkins et al. |
| 2014/0288358 A1 | 9/2014 | Puria et al. |
| 2015/0031941 A1 | 1/2015 | Perkins et al. |

FOREIGN PATENT DOCUMENTS

| | | |
|---|---|---|
| DE | 2044870 | 3/1972 |
| DE | 3243850 A1 | 5/1984 |
| DE | 3508830 A1 | 9/1986 |
| EP | 0 242 038 A2 | 10/1987 |
| EP | 0 291 325 A2 | 11/1988 |
| EP | 0 296 092 | 12/1988 |
| EP | 0 352 954 A2 | 1/1990 |
| EP | 1035753 A1 | 9/2000 |
| EP | 1435757 A1 | 7/2004 |
| EP | 1 845 919 A1 | 10/2007 |
| EP | 2272520 A1 | 1/2011 |
| FR | 2455820 | 11/1980 |
| GB | 2085694 A | 4/1982 |
| JP | 60-154800 | 8/1985 |
| JP | S621726 B2 | 1/1987 |
| JP | S63252174 A | 10/1988 |
| JP | 64-43252 A | 2/1989 |
| JP | 09-327098 | 12/1997 |
| JP | 2004193908 A | 7/2004 |
| JP | 2005516505 A | 6/2005 |
| JP | 2006-060833 A | 3/2006 |
| KR | 10-0624445 B1 | 9/2006 |
| WO | WO 92/09181 A1 | 5/1992 |
| WO | WO 97/36457 A1 | 10/1997 |
| WO | WO 97/45074 A1 | 12/1997 |
| WO | WO 98/06236 A1 | 2/1998 |
| WO | WO 99/03146 | 1/1999 |
| WO | WO 99/15111 | 4/1999 |
| WO | WO-0022875 A2 | 4/2000 |
| WO | WO-0022875 A3 | 7/2000 |
| WO | WO 01/50815 A1 | 7/2001 |
| WO | WO 01/58206 A2 | 8/2001 |
| WO | WO 02/39874 A2 | 5/2002 |
| WO | WO-03030772 A2 | 4/2003 |
| WO | WO 03/063542 A2 | 7/2003 |
| WO | WO 2004/010733 A1 | 1/2004 |
| WO | WO 2005/015952 | 2/2005 |
| WO | WO 2006/039146 A2 | 4/2006 |
| WO | WO 2006/042298 A2 | 4/2006 |
| WO | WO 2006/075169 | 7/2006 |
| WO | WO 2006/075175 | 7/2006 |
| WO | WO-2006071210 A1 | 7/2006 |
| WO | WO-2007023164 A1 | 3/2007 |
| WO | WO 2009/047370 A2 | 4/2009 |
| WO | WO 2009/056167 A1 | 5/2009 |
| WO | WO 2009/062142 A1 | 5/2009 |
| WO | WO 2009/125903 A1 | 10/2009 |
| WO | WO-2010147935 A1 | 12/2010 |
| WO | WO-2010148345 A2 | 12/2010 |

OTHER PUBLICATIONS

Athanassiou et al., "Laser controlled photomechanical actuation of photochromic polymers Microsystems" Rev. Adv. Mater. Sci., 2003; 5:245-251.

Ayatollahi et al., "Design and Modeling of Micromachined Condenser MEMS Loudspeaker using Permanent Magnet Neodymium-Iron-Boron (Nd—Fe—B)," IEEE International Conference on Semiconductor Electronics, 2006. ICSE '06, Oct. 29, 2006-Dec. 1, 2006; pp. 160-166.

(56) References Cited

OTHER PUBLICATIONS

Baer et al., "Effects of Low Pass Filtering on the Intelligibility of Speech in Noise for People With and Without Dead Regions at High Frequencies," J Acoust Soc Am. Sep. 2002;112(3 Pt 1):1133-1144.
Best et al., "Influence of High Frequencies on Speech Locatisation," Abstract 981, Feb. 24, 2003, retrieved from: http://www.aro.org/abstracts.html.
Birch et al., "Microengineered systems for the hearing impaired," IEE Colloquium on Medical Applications of Microengineering, Jan. 31, 1996; pp. 2/1-2/5.
Burkhard et al., "Anthropometric Manikin for Acoustic Research," J Acoust Soc. Am. Jul. 1975;58(1):214-22.
Camacho-Lopez et al., "Fast Liquid Crystal Elastomer Swims Into the Dark," Electronic Liquid Crystal Communications, (Nov. 26, 2003), 9 pages total.
Carlile et al., Abstract 1264—"Spatialisation of Talkers and the Segregation of Concurrent Speech ," Feb. 24, 2004, retrieved from: http://www.aro.org/archives/2004/2004_1264.html.
Cheng et al., "A Silicon Microspeaker for Hearing Instruments," Journal of Micromechanics and Microengineering 2004; 14(7):859-866.
Datskos et al., "Photoinduced and thermal stress in silicon microcantilevers", Applied Physics Letters, Oct. 19, 1998; 73(16):2319-2321.
Decraemer et al., "A Method for Determining Three-Dimensional Vibration in the Ear," *Hearing Research*, 77 (1-2): 19-37 (1994).
"EAR", Retrieved from the Internet: <<http://wwwmgs.bionet.nsc.ru/mgs/gnw/trrd/thesaurus/Se/ear.html>>, downloaded on Jun. 17, 2008, 4 pages total.
Fay, "Cat Ear Drum Mechanics," Ph.D. thesis, Dissertation submitted to Department of Aeronautics and Astronautics, Stanford University, May 2001, 210 pages total.
Fay et al., "Cat Eardrum Response Mechanics," in Calladine Festschrift, edited by S. Pellegrino (Kluwer Academic Publishers, The Netherlands, 10 pages total.
Fletcher, "Effects of Distortion on the Individual Speech Sounds", Chapter 18, *ASA Edition of Speech and Hearing in Communication*, Acoust Soc.of Am. (republished in 1995) pp. 415-423.
Freyman et al., "Spatial Release from Informational Masking in Speech Recognition," J Acoust Soc Am. May 2001;109(5 Pt 1):2112-2122.
Freyman et al., "The Role of Perceived Spatial Separation in the Unmasking of Speech," J Acoust Soc Am. Dec. 1999;106(6):3578-3588.
Gennum, GA3280 Preliminary Data Sheet: Voyageur TD Open Platform DSP System for Ultra Low Audio Processing, downloaded from the Internet: <<http://www.sounddesigntechnologies.com/products/pdf/37601DOC.pdf>>, Oct. 2006; 17 pages.
Gobin et al; "Comments on the physical basis of the active materials concept" Proc. SPIE 4512:84-92.
Hato et al., "Three-Dimensional Stapes Footplate Motion in Human Temporal Bones." Audiol Neurootol , 2003; 8: 140-152.
"Headphones" Wikipedia Entry, downloaded from the Internet : <<http://en.wikipedia.org/wiki/Headphones>>, downloaded on Oct. 27, 2008, 7 pages total.
Hofman et al., "Relearning Sound Localization With New Ears," Nat Neurosci. Sep. 1998;1(5):417-421.
Izzo et al., "Laser stimulation of the auditory nerve," Lasers Surg Med. Sep. 2006;38(8):745-753.
Izzo et al, "Laser stimulation of auditory neurons: effect of shorter pulse duration and penetration depth," Biophys J. Apr. 15, 2008;94(8):3159-3166.
Izzo et al., "Selectivity of neural stimulation in the auditory system: a comparison of optic and electric stimuli," J Biomed Opt. Mar.-Apr. 2007;12(2):021008.
Jin et al., "Speech Localization", J. Audio Eng. Soc. convention paper, presented at the AES 112th Convention, Munich, Germany, May 10-13, 2002, 13 pages total.

Killion, "Myths About Hearing Noise and Directional Microphones," *The Hearing Review*, vol. 11, No. 2, (Feb. 2004), pp. 14, 16, 18, 19, 72 & 73.
Killion, "SNR loss: I can hear what people say but I can't understand them," The Hearing Review, 1997; 4(12):8-14.
Lee et al., "A Novel Opto-Electromagnetic Actuator Coupled to the tympanic Membrane" Journal of Biomechanics, 2008; 41(16): 3515-3518.
Lee et al., "The Optimal Magnetic Force for a Novel Actuator Coupled to the Tympanic Membrane: A Finite Element Analysis," Biomedical Engineering: Applications, Basis and Communications, 2007; 19(3):171-177.
Lezal, "Chalcogenide glasses—survey and progress", J. Optoelectron Adv Mater., Mar. 2003; 5 (1):23-34.
Markoff, "Intuition + Money: An Aha Moment," New York Times Oct. 11, 2008, p. BU4, 3 pages total.
Martin et al. "Utility of Monaural Spectral Cues is Enhanced in the Presence of Cues to Sound-Source Lateral Angle," *JARO*, vol. 5, (2004), pp. 80-89.
Moore, "Loudness Perception and Intensity Resolution", *Cochlear Hearing Loss*, Whurr Publishers. Ltd., (1998), Chapter 4, pp. 90-115.
Murugasu et al., "Malleus-to-footplate versus malleus-to-stapes-head ossicular reconstruction prostheses: temporal bone presure gain measurements and clinical audiological data," Otol Neurotol. Jul. 2005;26(4):572-582.
Musicant et al., "Direction-Dependent Spectral Properties of Cat External Ear: New Data and Cross-Species Comparisons," J. Acostic. Soc. Am, May 10-13, 2002, Feb. 1990; 8(2):757-781.
National Semiconductor, LM4673 Boomer: Filterless, 2.65W, Mono, Class D Audio Power Amplifier, [Data Sheet] downloaded from the Internet: <<http://www.national.com/ds/LM/LM4673.pdf>>; Nov. 1, 2007; 24 pages.
O'Connor et al., "Middle ear cavity and ear canal pressure-driven stapes velocity responses in human cadaveric temporal bones," J Acoust Soc Am. Sep. 2006;120(3):1517-28.
Perkins et al., "The EarLens System: New sound transduction methods," Hear Res. Feb. 2, 2010; 10 pages total.
Poosanaas et al., "Influence of sample thickness on the performance of photostrictive ceramics," J. App. Phys., Aug. 1, 1998, 84(3):1508-1512.
Puria et al., "Abstract 1112: A gear in the middle ear," ARO Thirtieth Annual MWM, Denver CO, Feb. 13, 2007.
Puria et al., "Malleus-to-footplate ossicular reconstruction prosthesis positioning: cochleovestibular pressure optimization", Otol Neurotol. May 2005;26(3):368-379.
Puria and Allen, "Measurements and Model of the Cat Middle Ear: Evidence of Tympanic Membrane Acoustic Delay," *Journal of the Acoustical Society of America*, 104 (6): 3463-3481 (1998).
Puria et al., "Middle Ear Morphometry From Cadaveric Temporal Bone MicroCT Imaging," Proceedings of the 4th International Symposium, Zurich, Switzerland, Jul. 27-30, 2006, Middle Ear Mechanics in Research and Otology, pp. 259-268.
Puria et al., "Sound-Pressure Measurements in The Cochlear Vestibule of Human-Cadaver Ears," *Journal of the Acoustical Society of America*, 101 (5-1): 2754-2770, (1997).
Roush, "SiOnyx Brings "Black Silicon" into the Light; Material Could Upend Solar, Imaging Industries," Xconomy, Oct. 12, 2008, retrieved from the Internet: <<http://www.xconomy.com/boston/2008/10/12/sionyx-brings-black-silicon-into-the-light-material-could-upend-solar-imaging-industries/>> 4 pages total.
Rubinstein, "How Cochlear Implants Encode Speech," Curr Opin Otolaryngol Head Neck Surg. Oct. 2004;12(5):444-8; retrieved from the Internet: <http://www.ohsu.edu/nod/documents/week3/Rubenstein.pdf>.
Sekaric et al., "Nanomechanical resonant structures as tunable passive modulators," *App. Phys. Lett.*, vol. 80, No. 19, (Nov. 2003), pp. 3617-3619.
Sound Design Technologies, "Voyager TD™ Open Platform DSP System for Ultra Low Power Audio Processing—GA3280 Data Sheet", Oct. 2007; retrieved from the Internet: <<http://www.sounddes.com/pdf/37601DOC.pdf>>, 15 page total.

(56) References Cited

OTHER PUBLICATIONS

Shaw, "Transformation of Sound Pressure Level From the Free Field to the Eardrum in the Horizontal Plane," J. Acoust. Soc. Am., Dec. 1974; 56(6):1848-1861.
Shih, "Shape and displacement control of beams with various boundary conditions via photostrictive optical actuators," Proc. IMECE (Nov. 2003), pp. 1-10.
Shock, "How deep brain stimulation works for Parkinson's Disease" [website]; retrieved from the Internet: <http://www.shockmd.com/2009/05/11/how-deep-brain-stimulation-works-for-parkinsons-disease/> on Jun. 18, 2010, 6 pages total.
Stenfelt et al., "Bone-Conducted Sound: Physiological and Clinical Aspects," Otology & Neurotology, Nov. 2005; 26 (6):1245-1261.
Stuchlik et al, "Micro-nano actuators driven by polarized light", IEEE Proc. Sci. Meas. Techn. Mar. 2004, 151(2):131-136.
Suski et al., "Optically activated ZnO/SiO2/Si cantilever beams", Sensors & Actuators, 1990; 24:221-225.
Takagi et.al.; "Mechanochemical Synthesis of Piezoelectric PLZT Powder", *KONA*, 2003, 151(21):234-241.
Thakoor et al., "Optical microactuation in piezoceramics", Proc. SPIE, Jul. 1998; 3328:376-391.
Tzou et al; "Smart Materials, Precision Sensors/Actuators, Smart Structures, and Structronic Systems", *Mechanics of Advanced Materials and Structures*, 2004;11:367-393.
Uchino et al.; "Photostricitve actuators," *Ferroelectrics* 2001; 258:147-158.
Vickers et al., "Effects of Low-Pass Filtering on the Intelligibility of Speech in Quiet for People With and Without Dead Regions at High Frequencies," *J Acoust Soc Am*. Aug. 2001;110(2):1164-1175.
Vinikman-Pinhasi et al., "Piezoelectric and piezooptic effects in porous silicon," Applied Physics Letters, Mar. 2006; 88(11): 111905-111906.
Wang et al., "Preliminary Assessment of Remote Photoelectric Excitation of an Actuator for a Hearing Implant," Proceeding of the 2005 IEEE, Engineering in Medicine and Biology 27th Annual Conference, Shanghai, China, Sep. 1-4, 2005, pp. 6233-6234.
Wiener et al., "On the Sound Pressure Transformation by the Head and Auditory Meatus of the Cat", Acta Otolaryngol. Mar. 1966;61(3):255-269.
Wightman et al., "Monaural Sound Localization Revisited," J Acoust Soc Am. Feb. 1997;101(2):1050-1063.
Yi et al., "Piezoelectric Microspeaker with Compressive Nitride Diaphragm," The Fifteenth IEEE International Conference on Micro Electro Mechanical Systems, 2002; pp. 260-263.
Yu et al. "Directed bending of a polymer film by light", Nature, Sep. 2003; 425(6954):145.
International Search Report and Written Opinion of PCT Application No. PCT/US2010/039209, dated Sep. 28, 2010, 17 pages total.
U.S. Appl. No. 60/702,532, filed Jul. 25, 2005, inventor: Nikolai Aljuri.
U.S. Appl. No. 61/099,087, filed Sep. 22, 2008, inventor: Paul Rucker.
International search report dated Mar. 29, 2011 for PCT/US2010/039776.
Office action dated Aug. 3, 2012 for U.S. Appl. No. 12/822,810.
Office action dated Feb. 25, 2013 for U.S. Appl. No. 12/822,810.
Office action dated Sep. 12, 2013 for U.S. Appl. No. 12/822,810.
Notice of allowance dated Jul. 2, 2014 for U.S. Appl. No. 12/822,810.
Dictionary.com's (via American Heritage Medical Dictionary) online dictionary definition of 'percutaneous'. Accessed on Jun. 3, 2013. 2 pages.
Merriam-Webster's online dictionary definition of 'percutaneous'. Accessed on Jun. 3, 2013. 3 pages.
Fay, et al. Preliminary evaluation of a light-based contact hearing device for the hearing impaired. Otol Neurotol. Jul. 2013;34(5):912-21. doi: 10.1097/MAO.0b013e31827de4b1.
Fritsch, et al. EarLens transducer behavior in high-field strength MRI scanners. Otolaryngol Head Neck Surg. Mar. 2009;140(3):426-8. doi: 10.1016/j.otohns.2008.10.016.
Gantz, et al. Broad Spectrum Amplification with a Light Driven Hearing System. Combined Otolaryngology Spring Meetings, 2016 (Chicago).
Gantz, et al. Light Driven Hearing Aid: A Multi-Center Clinical Study. Association for Research in Otolaryngology Annual Meeting, 2016 (San Diego).
Gantz, et al. Light-Driven Contact Hearing Aid for Broad Spectrum Amplification: Safety and Effectiveness Pivotal Study. Otology & Neurotology Journal, 2016 (in review).
Hakansson, et al. Percutaneous vs. transcutaneous transducers for hearing by direct bone conduction (Abstract). Otolaryngol Head Neck Surg. Apr. 1990;102(4):339-44.
Jian, et al. A 0.6 V, 1.66 mW energy harvester and audio driver for tympanic membrane transducer with wirelessly optical signal and power transfer. InCircuits and Systems (ISCAS), 2014 IEEE International Symposium on Jun. 1, 2014. 874-7. IEEE.
Khaleghi, et al. Characterization of Ear-Canal Feedback Pressure due to Umbo-Drive Forces: Finite-Element vs. Circuit Models. ARO Midwinter Meeting 2016, (San Diego).
Levy, et al. Characterization of the available feedback gain margin at two device microphone locations, in the fossa triangularis and Behind the Ear, for the light-based contact hearing device. Acoustical Society of America (ASA) meeting, 2013 (San Francisco).
Levy, et al. Extended High-Frequency Bandwidth Improves Speech Reception in the Presence of Spatially Separated Masking Speech. Ear Hear. Sep.-Oct. 2015;36(5):e214-24. doi: 10.1097/AUD.0000000000000161.
MAH. Fundamentals of photovoltaic materials. National Solar Power Research Institute. Dec. 21, 1998, 3-9.
Moore, et al. Spectro-temporal characteristics of speech at high frequencies, and the potential for restoration of audibility to people with mild-to-moderate hearing loss. Ear Hear. Dec. 2008;29(6):907-22. doi: 10.1097/AUD.0b013e31818246f6.
Perkins, et al. Light-based Contact Hearing Device: Characterization of available Feedback Gain Margin at two device microphone locations. Presented at AAO-HNSF Annual Meeting, 2013 (Vancouver).
Perkins, et al. The EarLens Photonic Transducer: Extended bandwidth. Presented at AAO-HNSF Annual Meeting, 2011 (San Francisco).
Perkins, R. Earlens tympanic contact transducer: a new method of sound transduction to the human ear. Otolaryngol Head Neck Surg. Jun. 1996;114(6):720-8.
Puria, et al. Cues above 4 kilohertz can improve spatially separated speech recognition. The Journal of the Acoustical Society of America, 2011, 129, 2384.
Puria, et al. Extending bandwidth above 4 kHz improves speech understanding in the presence of masking speech. Association for Research in Otolaryngology Annual Meeting, 2012 (San Diego).
Puria, et al. Extending bandwidth provides the brain what it needs to improve hearing in noise. First international conference on cognitive hearing science for communication, 2011 (Linkoping, Sweden).
Puria, et al. Hearing Restoration: Improved Multi-talker Speech Understanding. 5th International Symposium on Middle Ear Mechanics in Research and Otology (MEMRO), Jun. 2009 (Stanford University).
Puria, et al. Imaging, Physiology and Biomechanics of the middle ear: Towards understating the functional consequences of anatomy. Stanford Mechanics and Computation Symposium, 2005, ed Fong J.
Puria, et al. Temporal-Bone Measurements of the Maximum Equivalent Pressure Output and Maximum Stable Gain of a Light-Driven Hearing System That Mechanically Stimulates the Umbo. Otol Neurotol. Feb. 2016;37(2):160-6. doi: 10.1097/MAO.0000000000000941.
Puria, et al. The EarLens Photonic Hearing Aid. Association for Research in Otolaryngology Annual Meeting, 2012 (San Diego).
Puria, et al. The Effects of bandwidth and microphone location on understanding of masked speech by normal-hearing and hearing-impaired listeners. International Conference for Hearing Aid Research (IHCON) meeting, 2012 (Tahoe City).

(56) References Cited

OTHER PUBLICATIONS

Puria. Measurements of human middle ear forward and reverse acoustics: implications for otoacoustic emissions. J Acoust Soc Am. May 2003;113(5):2773-89.

Puria, S. Middle Ear Hearing Devices. Chapter 10. Part of the series Springer Handbook of Auditory Research pp. 273-308. Date: Feb. 9, 2013.

Robles, et al. Mechanics of the mammalian cochlea. Physiol Rev. Jul. 2001;81(3):1305-52.

Song, et al. The development of a non-surgical direct drive hearing device with a wireless actuator coupled to the tympanic membrane. Applied Acoustics. Dec. 31, 2013;74(12):1511-8.

Web Books Publishing, "The Ear," accessed online Jan. 22, 2013, available online Nov. 2, 2007 at http://www.web-books.com/eLibrary/Medicine/Physiology/Ear/Ear.htm.

Dundas et al. The Earlens Light-Driven Hearing Aid: Top 10 questions and answers. Hearing Review. 2018;25(2):36-39.

Gantz, et al. Light-Driven Contact Hearing Aid for Broad-Spectrum Amplification: Safety and Effectiveness Pivotal Study. Otology & Neurotology. Copyright 2016. 7 pages.

Khaleghi, et al. Attenuating the ear canal feedback pressure of a laser-driven hearing aid. J Acoust Soc Am. Mar. 2017;141(3):1683.

Khaleghi et al. Attenuating the feedback pressure of a light-activated hearing device to allows microphone placement at the ear canal entrance. IHCON 2016, International Hearing Aid Research Conference, Tahoe City, CA, Aug. 2016.

Khaleghi et al. Mechano-Electro-Magnetic Finite Element Model of a Balanced Armature Transducer for a Contact Hearing Aid. Proc. MoH 2017, Mechanics of Hearing workshop, Brock University, Jun. 2017.

Khaleghi et al. Multiphysics Finite Element Model of a Balanced Armature Transducer used in a Contact Hearing Device. ARO 2017, 40th ARO MidWinter Meeting, Baltimore, MD, Feb. 2017.

Levy et al. Light-driven contact hearing aid: a removable direct-drive hearing device option for mild to severe sensorineural hearing impairment. Conference on Implantable Auditory Prostheses, Tahoe City, CA, Jul. 2017. 1 page.

McElveen et al. Overcoming High-Frequency Limitations of Air Conduction Hearing Devices Using a Light-Driven Contact Hearing Aid. Poster presentation at The Triological Society, 120th Annual Meeting at COSM, Apr. 28, 2017; San Diego, CA.

Struck, et al. Comparison of Real-world Bandwidth in Hearing Aids vs Earlens Light-driven Hearing Aid System. The Hearing Review. TechTopic: EarLens. Hearingreview.com. Mar. 14, 2017. pp. 24-28.

\* cited by examiner

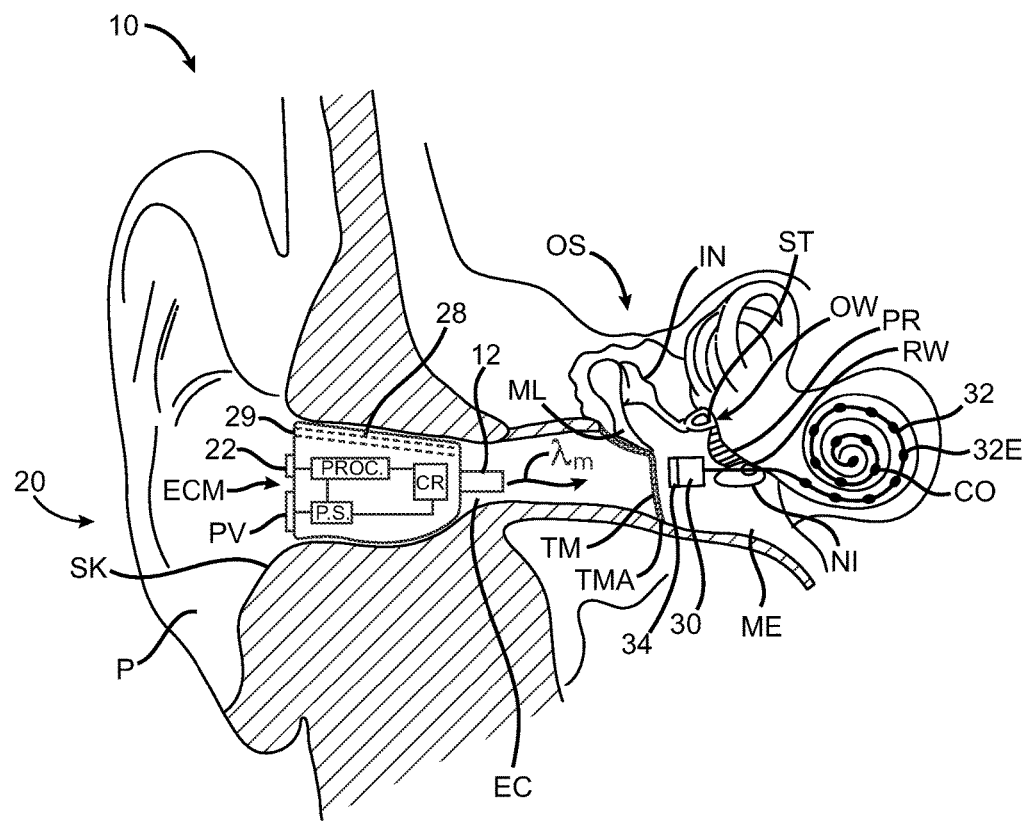
FIG. 1A1

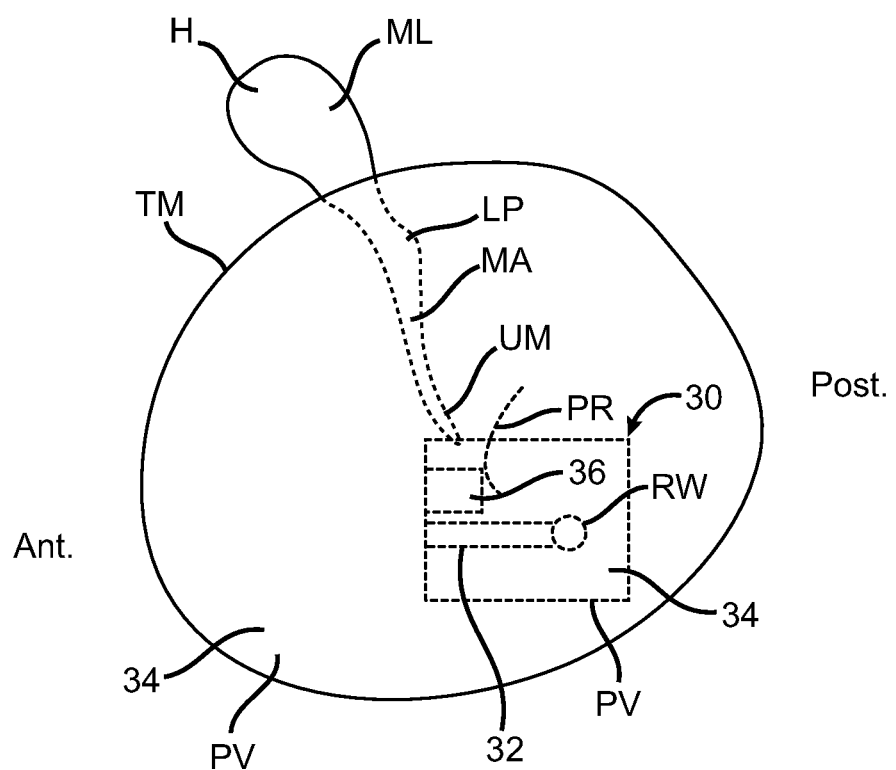
FIG. 1A2

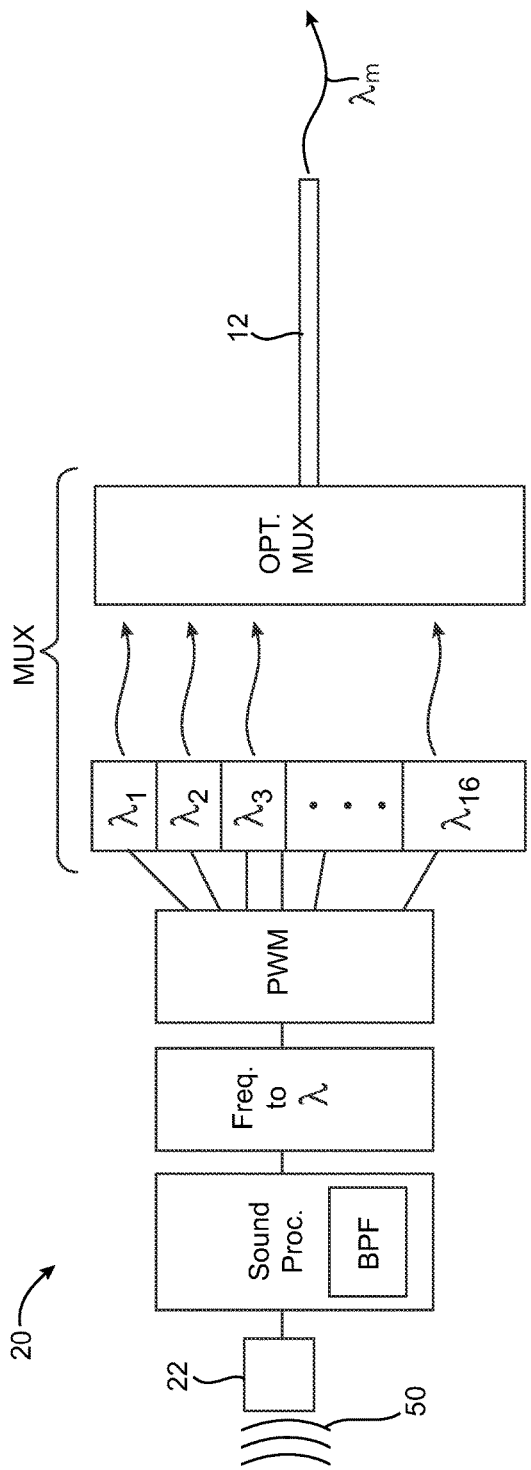
FIG. 2A
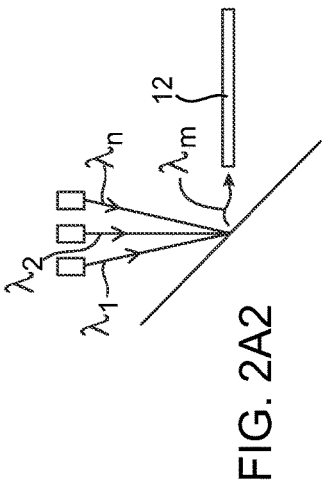
FIG. 2A2
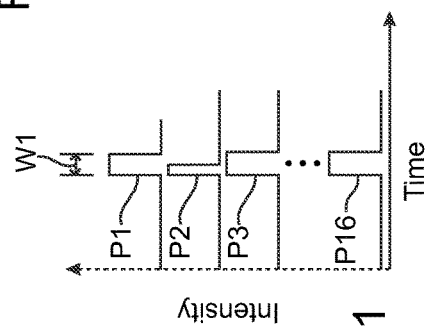
FIG. 2A1

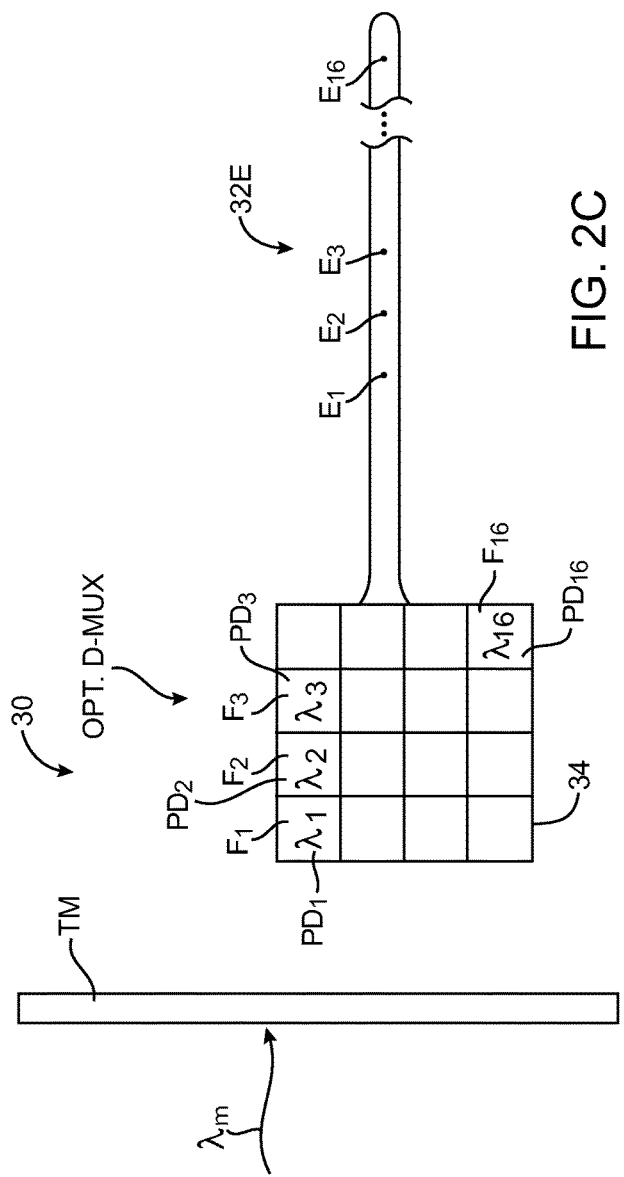
FIG. 2C
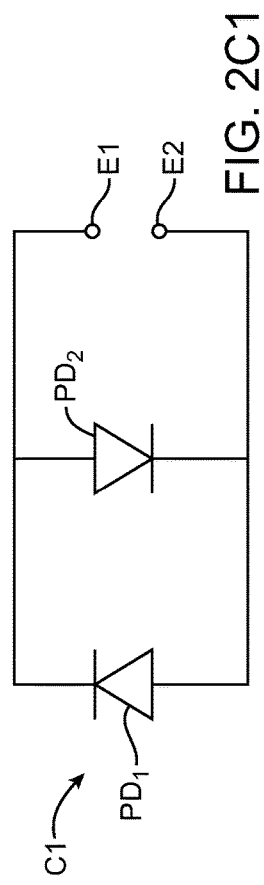
FIG. 2C1

OPTICALLY COUPLED COCHLEAR IMPLANT SYSTEMS AND METHODS

CROSS-REFERENCES TO RELATED APPLICATIONS

The present non-provisional application claims priority to U.S. Pat. App. Ser. No. 61/218,377 filed 18 Jun. 2009, entitled "Optically Coupled Cochlear Implant Systems and Methods"; and U.S. Pat. App. Ser. No. 61/220,124 filed on 24 Jun. 2009, entitled "Transdermal Photonic Energy Transmission Device and Methods"; the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

Field of the Invention

The present invention relates to tissue stimulation with electrodes generally, and more specifically to stimulation of the cochlea for hearing. Although specific reference is made to cochlear implants, embodiments of the present invention can be used in many applications wherein tissue is stimulated, for example with stimulation of muscles, nerves and neural tissue, for example the treatment of Parkinson's.

The prior devices used to stimulate tissue can be somewhat invasive, in at least some instances. An example of a device used to stimulate tissue is the cochlear implant, which can be used to stimulate the nerve tissue of the cochlea. At least some of the prior devices used with cochlear implants can be more invasive than would be ideal. For example, in at least some instances cochlear implants rely on the cutting of bone and the cut bone can take at least some time to heal such that the surgery can be more invasive than would be ideal. Also, the cutting of bone may lead to weakening of the bone in at least some instances. Also, at least some of the prior cochlear implants may be removed and the cut bone may leave at least a partial void in the bone in at least some instances. Also, the circuitry associated with cochlear implants can be somewhat larger than ideal.

The coupling of cochlear implants to an external driver can be somewhat cumbersome and may be less than ideal in at least some instances. For example, prior cochlear implants can transmit energy through a pair of transmitter and receiver RF coils, and the use of such coils can be somewhat awkward and less than ideal in at least some instances. For example, the coils may require alignment and although a pair of magnets may be used to align the RF coils, one of the two magnets may be semi-permanently implanted in temporal bones which can be somewhat invasive in at least some instances. As body implanted magnets are contraindications for MRI machines, and the magnets may be surgically removed prior to imaging in at least some instances. As cochlear implants can be implanted in children as young as 18 months and implanted in adults, there is at least a reasonable likelihood that the surgically implanted magnets may require removal prior to an MRI and a second procedure for reimplantation following the MRI in at least some instances.

At least some of the prior cochlear implants may produce a perceived sound quality that is less than ideal in at least some instances. For example, sound localization cues and allow a person to localize sound and hear in a noisy environment, and in at least some instances the prior cochlear implant devices may not provide the sound localization cues that are present with natural hearing. Also, the sound produced with at least some cochlear implant devices may sound at least somewhat distorted in at least some instances.

It would be helpful to stimulate tissue with electrical current in a manner that overcomes at least some of the shortcomings of the prior cochlear implant devices. Ideally, such devices would be less invasive and provide improved hearing with sound localization cues and less distortion land fewer surgeries after implantation.

SUMMARY OF THE INVENTION

The present invention relates to tissue stimulation with electrodes generally, and more specifically to stimulation of the cochlea for hearing. Although specific reference is made to cochlear implants, embodiments of the present invention can be used in many applications wherein tissue is stimulated, for example with stimulation of muscles, nerves and neural tissue, for example the treatment of Parkinson's.

Embodiments of the present invention provide devices, systems and methods of stimulating tissue with electrical current that overcome at least some of the problems associated with the prior devices. For example, an output assembly can be sized for placement in the middle and inner ear, such that removal of bone can be decreased. Also, the output assembly may comprise substantially non-magnetic materials such that a person can undergo MRI imaging when the output assembly is implanted. The output assembly may comprise at least one photo detector, a demultiplexer and an electrode array sized to pass through an incision in the eardrum. An input transducer assembly can be configured to transmit a multiplexed optical signal to the output assembly. For example, the input assembly can be configured to transmit the multiplexed optical signal through the eardrum such that tissue removal can be decreased and the device can be implanted without removal of bone. The multiplexed optical signal may comprise a pulse width modulated signal so as to decrease the effect of non-linearities of the light source and light detector and provide quality sound to the user. For example, the pulse width modulated signal may comprise optical pulses having a frequency above the hearing frequency, for example above at least about 20 kHz, such that the cochlea demodulates pulses and the phase of the sound signal transmitted to the user is substantially maintained. The sound may comprise a plurality of frequencies corresponding a plurality of channels, and a series of width modulated pulses may be determined for each of the channels. The width modulated pulses of each channel can be delivered optically through the tympanic membrane with high frequencies such that the cochlea demodulates the high frequency pulses to the user perceptible sound having amplitude and phase maintained.

In a first aspect, embodiments of the present invention provide a method of stimulating tissue. A multiplexed optical signal is transmitted so as to stimulate the tissue.

In another aspect, embodiments of the present invention provide a method of transmitting a sound to a cochlea of a user, the user having a tissue, the method comprising: transmitting a multiplexed optical signal through the tissue of the user such that the user hears the sound in response to the multiplexed optical signal transmitted through the tissue.

In many embodiments, the tissue comprises tissue of an eardrum.

In many embodiments, the multiplexed optical signal is transmitted to an optical structure supported with the middle ear, the optical structure configured to separate wavelengths of the multiplexed signal to stimulate the cochlea.

In many embodiments, the said optical structure is affixed to the middle ear. The said optical structure can be sized to pass through an incision in the eardrum for placement in a cavity of the middle ear.

In many embodiments, the optical structure comprises at least one of an optical filter, an optical fiber, a grating, an etalon, a plurality of optical fibers, a waveguide, a plurality of waveguides, a mirror or a prism.

In many embodiments, the multiplexed optical signal comprises a plurality of channels, each channel of the plurality corresponding to at least one frequency of the sound.

In many embodiments, the plurality of channels corresponds to at least about sixteen channels and said at least one frequency corresponds to at least about sixteen frequencies.

In many embodiments, the multiplexed optical signal is transmitted through the eardrum with a plurality of light sources, each light source configured to transmit a light signal corresponding to said channel of the plurality such that said light source corresponds to said at least one frequency of sound. The plurality of light sources may comprise at least three light sources, and each of the at least three light sources is configured to emit separate wavelengths of light.

In many embodiments, each of the plurality of channels corresponds to a pair of electrodes, and a first current travels between said pair of electrodes in response to a first width modulated light pulse and a second current travels between said pair of electrodes in response to a second width modulated light pulse. The first current is opposite the second current. The first current has a first amount corresponding to a first width of the first pulse, and the second current has a second amount corresponding to a second width of the second pulse. The width of the first pulse corresponds to the width of the second pulse so as to inhibit rectification and balance charge transfer between the first electrode and the second electrode.

In many embodiments, the first light pulse comprises a first wavelength of light coupled to a first detector and the second light pulse comprises a second wavelength of light coupled to a second detector.

In many embodiments, the multiplexed optical signal is transmitted through the eardrum of the user to at least one photodetector, and the at least one photodetector affixed to the middle ear and coupled to an electrode array positioned at least partially within the cochlea. The at least one photodetector and at least one electrode array can be sized to pass through an incision in the eardrum.

In many embodiments, the multiplexed optical signal comprises a wavelength multiplexed optical signal, the wavelength multiplexed optical signal comprising a plurality of wavelengths such that each wavelength corresponds to an electrode of the array. Each wavelength of the plurality may correspond to an electrode of the array.

In many embodiments, the at least one photodetector comprises a plurality of photodetectors, and each photodetector of the plurality is coupled to a corresponding electrode of the array and a corresponding wavelength of the plurality such that the tissue stimulating current is passed through the electrode in response to the tissue stimulating wavelength.

In many embodiments, an optical structure is positioned in the middle ear of the user to separate the wavelengths to correspond with each detector, and such that each separated wavelength corresponding to each detector is transmitted to said each detector based on the wavelength.

In many embodiments, a plurality of optical filters is positioned in the middle ear of the user, and the wavelengths are separated with the optical filters, in which each optical filter is positioned over one detector and configured to pass the wavelengths corresponding to the electrode coupled to said one detector.

In many embodiments, a grating is configured to select the wavelengths of each detector to corresponding to each electrode.

In many embodiments, the multiplexed optical signal comprises a time division multiplexed signal. The time division multiplexed signal may comprise the plurality of time-slots, in which each time slot of the plurality corresponds to an electrode of the array. The time division multiplexed signal may comprise the plurality of time slots and a clock signal, and the circuitry can be coupled to the at least one photodetector and the electrode array so as to receive the clock signal and divide the time division multiplexed signal among the electrodes of the array such that each time slot corresponds to at least one electrode of the array.

In many embodiments, each time slot corresponds to at least one frequency of the sound such that current is passed through each electrode in response to a portion of the multiplexed signal corresponding to the time slot. The time division multiplexed signal can pulse width modulated such that each timeslot of the plurality comprises a pulse of light having a duration that corresponds to current through the electrode corresponding to said timeslot.

In many embodiments, the multiplexed optical signal is transmitted to at least one optical fiber extending into the cochlea. The at least one optical fiber can be sized to pass through an incision in the middle ear. The at least one optical fiber may comprise a plurality of optical fibers extending into the cochlea, each fiber corresponding to at least one frequency of the sound. Each fiber can be configured to stimulate the cochlea at a predetermined location of the cochlea corresponding to a corresponding range of frequencies in response to the at least one frequency of the sound.

In many embodiments, the multiplexed optical signal is transmitted through at least one of an opening or a window in the eardrum.

In many embodiments, the electrode array, the at least one photodetector, and the demultiplexer comprise substantially non-magnetic materials configured for MRI imaging when implanted in the user.

In many embodiments, the sound comprises a phase, and the optical signal comprises width modulated light pulses transmitted with a frequency of at least about 10 kHz. Each light pulse generates an electrical current within the cochlea such that the cochlea demodulates the light pulses and the phase of the sound is maintained.

In many embodiments, the width modulated light pulses comprises a series of width modulated pulses for each channel and wherein the series of width modulated pulses of said each channel comprises a frequency of at least about 10 kHz to maintain the phase of the sound when the user hears the sound. The frequency of said each series may comprise at least about 20 kHz to maintain the phase of the sound when the user hears the sound. The plurality of channels may comprise at least about eight channels and the frequency of the width modulated light pulses comprises at least about 160 kHz.

In many embodiments, the pulses of the series of width modulated pulses of each channel are combined to form a sequence of packet of pulses, each packet comprising one pulse from each series.

In many embodiments, the at least one photodetector is positioned in the middle ear cavity so as to receive the multiplexed optical signal through a posterior portion of the eardrum.

In another aspect, embodiments of the present invention provide a system to stimulate tissue. A plurality of electrodes is configured for placement at least partially within the tissue. Circuitry is configured to receive a signal from a source. At least one light source coupled to the circuitry and configured to emit a multiplexed optical signal comprising a plurality of light pulses. At least one photo detector is configured to receive the multiplexed optical and pass current through the electrodes in response to the light pulses to stimulate the tissue.

In another aspect, embodiments of the present invention provide a system to transmit an audio signal to a user. An electrode array comprises a plurality of electrodes configured for placement at least partially within a cochlea of the user. Circuitry is configured to receive the audio signal from a sound source. At least one light source coupled to the circuitry and configured to emit a multiplexed optical signal comprising a plurality of light pulses. At least one detector is configured to receive the multiplexed optical and pass current through the electrodes in response to the light pulses.

In many embodiments, the circuitry is configured to determine widths of a plurality of light pulses and wherein each light pulse corresponds to an electrode of the array and a width of said each light pulse corresponds to an amount of current through said corresponding electrode of the array.

In many embodiments, the circuitry is configured to determine frequencies of the audio signal and wherein the frequencies correspond to electrodes of the array and wherein the circuitry is configured to determine a width of each pulse in response to one or more of the frequencies.

In many embodiments, the at least one light source comprises a plurality of light sources and wherein each light source corresponds to one electrode of the array. Each of the plurality of light sources can be configured to emit light comprising wavelengths substantially separated from wavelengths of other light sources of the plurality.

In many embodiments, the plurality of light sources comprises at least three light sources and the electrode array comprises at least three electrodes, and each of the at least three light sources corresponds to one electrode of the at least three electrodes of the array. Each of the at least three light sources can be configured to emit light comprising wavelengths substantially separated from others of the at least three light sources, and the wavelengths of each source correspond to one electrode of the at least three.

In many embodiments, the at least one detector comprises a plurality of detectors, and each detector of the plurality corresponds to one electrode of the array.

In many embodiments, the plurality of light detectors comprises at least three light detectors and the electrode array comprises at least three electrodes and each of the at least three light detectors corresponds to one electrode of the at least three electrodes of the array.

In many embodiments, an optical structure configured to receive the multiplexed optical signal, the optical structure configured for placement in the middle, the optical structure configured to select wavelengths of the multiplexed signal. The said optical structure can be sized to pass through an incision in the eardrum for placement in the middle ear and the electrode array is sized for placement at least partially inside the cochlea through a round window of the cochlea.

In many embodiments, the optical structure comprises at least one of an optical filter, a grating, an etalon, a plurality of optical fibers, or a prism.

In many embodiments, the multiplexed optical signal comprises a plurality of optical channels, each optical channel of the plurality corresponding to at least one frequency of the sound. The plurality of optical channels may correspond to at least about sixteen channels and said at least one frequency corresponds to at least about sixteen frequencies.

An elongate optical transmission structure is configured for placement at least partially within the ear canal of the user, and the elongate optical transmission structure is configured to transmit multiplexed optical signal through the eardrum.

In many embodiments, the multiplexed optical signal is transmitted through the eardrum of the user to at least one photodetector, in which the at least one photodetector is affixed to the middle ear and coupled to an electrode array positioned at least partially within the cochlea.

In many embodiments, the at least one photodetector and the electrode array are sized to pass through an incision in the eardrum.

In many embodiments, the multiplexed optical signal comprises a wavelength multiplexed optical signal, the wavelength multiplexed optical signal comprising a plurality of wavelengths such that each wavelength corresponds to an electrode of the array. Each wavelength of the plurality may correspond to an electrode of the array. The plurality of wavelengths may comprise at least three wavelengths and wherein the plurality of electrodes comprises at least three electrodes and wherein each wavelength of the plurality corresponds to one electrode of the at least three electrodes.

In many embodiments, the circuitry is configured to transmit a series of the light pulses to correspond to electrodes of the array.

In many embodiments, the series comprises a plurality of pulses and wherein each pulse of the plurality corresponds to one electrode of the plurality.

In many embodiments, the plurality of electrodes comprises at least three electrodes and wherein the series comprises at least three pulses and wherein each pulse of the at least three pulses corresponds to one electrode of the at least three electrodes.

In many embodiments, the series comprises a timing pulse. The timing pulse may comprise a substantially fixed width and wherein the timing pulse comprises energy to power circuitry coupled to the plurality of electrodes. Switching circuitry can be coupled to the at least one detector to couple sequentially each electrode of the plurality to the at least one detector in response to the timing pulse such that each pulse of the series corresponds to one electrode of the plurality. The series of pulses may comprise a pre-determined order and timing of the pulses and the switching circuitry may comprise a timer coupled to switches to open the switches and close the to correspond with pulses of the series.

In many embodiments, the series comprises at least three pulses and wherein the switching circuitry is configured to coupled at least one detector sequentially to each electrode of the at least three such that each pulse of the series corresponds to one electrode of the plurality.

In many embodiments, the electrode array, the at least one photodetector, and the demultiplexer comprise substantially non-magnetic materials configured for MRI imaging when implanted in the user.

In many embodiments, each of the plurality of channels corresponds to a pair of electrodes and wherein a first current travels between said pair of electrodes in response to a first width modulated light pulse and a second current travels between said pair of electrodes in response to a second width modulated light pulse, the first current opposite the second current, the first current opposite the second current, the first current having a first amount corresponding to a first width of the first pulse and the second current having a second amount corresponding to a second width the second pulse, and the width of the first pulse corresponds to the width of the second pulse so as to inhibit rectification and balance charge transfer between the first electrode and the second electrode.

In many embodiments, the first light pulse comprises a first wavelength of light coupled to a first detector coupled to said pair of electrodes, and the second light pulse comprises a second wavelength of light coupled to a second detector coupled to said pair of electrodes. The first detector is coupled to said pair of electrodes opposite the second detector. Each channel may correspond to a pair of electrodes and a first detector coupled to the pair of electrodes opposite a second detector, for example at least about 8 channels corresponding to 8 pairs of electrodes coupled 16 detectors.

In many embodiments, the sound comprises a phase and wherein the optical signal comprises width modulated light pulses transmitted with a frequency of at least about 10 kHz and wherein each light pulse generates an electrical current within the cochlea such that the cochlea demodulates the light pulses and the phase of the sound is maintained. The width modulated light pulses may comprise a series of width modulated pulses for each channel, and the series of width modulated pulses of said each channel comprises a frequency of at least about 10 kHz to maintain the phase of the sound when the user hears the sound.

In many embodiments, the frequency of said each series comprises at least about 20 kHz to maintain the phase of the sound when the user hears the sound.

In many embodiments, the plurality of channels comprises at least about eight channels and the frequency of the width modulated light pulses comprises at least about 160 kHz.

In many embodiments, the pulses of the series of width modulated pulses of each channel are combined to form a sequence of packet of pulses, each packet comprising one pulse from each series.

In another aspect, embodiments of the present invention provide a method of providing a hearing prosthesis for a user. An incision is made in an eardrum of the user, in which the eardrum comprises an annulus. An electrode array, at least one photodetector, and a demultiplexer are passed through the incision. For example, an output assembly may comprise the electrode array, the at least one photodetector, and the demultiplexer, and the output assembly can be passed through the incision.

In many embodiments, the incision extends at least partially through the annulus.

In many embodiments, the eardrum is positioned to a side of an ear canal to pass the electrode array, the demultiplexer and the at least one photodetector through the incision.

In many embodiments, the at least one detector and the demultiplexer are affixed to the middle ear of the user.

In many embodiments, the electrode array is positioned at least partially through a round window and wherein the at least one detector and the demultiplexer are positioned in a middle ear of the user.

In many embodiments, the at least one detector and the demultiplexer are affixed to the middle ear of the user.

In many embodiments, the at least one photo detector comprises at least three photo detectors.

In many embodiments, the demultiplexer comprises an optical demultiplexer. The optical demultiplexer may comprise at least three filters to separate at least three wavelengths of light.

In many embodiments, the demultiplexer comprises switching circuitry and a timer.

In many embodiments, the electrode array, the at least one photodetector, and the demultiplexer passed through the incision comprise substantially non-magnetic materials configured for MRI imaging.

In many embodiments, the at least one photodetector is positioned in the middle ear cavity to receive light energy transmitted through the posterior portion of the eardrum.

In another aspect, embodiments of the present invention provide a device to stimulate tissue. The device comprises a means for generating a multiplexed optical signal, and means for stimulating tissue in response to the optical signal. The means for generating the optical signal may comprise one or more of the structures of the input assembly for generating the multiplexed optical signals as described herein, and the means for stimulating the tissue may comprise one or more of the structures of the output assembly having the corresponding function as described herein.

BRIEF DESCRIPTION OF THE DRAWINGS

FIG. 1A1 shows an optically coupled cochlear implant system comprising an ear canal module, in accordance with embodiments of the present invention;

FIG. 1A2 shows an optically coupled output transducer assembly having a photodetector positioned in a middle ear cavity to couple optically through a posterior portion of the eardrum and an electrode array extending into the cochlea through the round window, as seen from the ear canal looking into the middle ear cavity with a medial view, in accordance with embodiments;

FIG. 2A shows an input transducer assembly configured to emit a wavelength multiplexed optical signal in accordance with embodiments of the present invention;

FIG. 2A1 optical pulses comprising separate wavelengths of light of a wavelength multiplexed optical signal as in FIG. 2A;

FIG. 2A2 shows an optical multiplexer configured to wavelength multiplex light from a plurality of light sources having separate wavelengths, as in FIG. 2A;

FIG. 2C shows an output transducer assembly comprising an optical demultiplexer comprising optical filters and an array of detectors, in accordance with embodiments;

FIG. 2C1 shows circuitry of a channel of the output transducer assembly of FIG. 2C so as to provide at least biphasic pulses in response to a first light pulse comprising a first wavelength and a second light pulse comprising a second wavelength, in accordance with embodiments;

FIG. 3A1 optical pulses comprising a series of pulses of the time multiplexed optical signal as in FIG. 3A;

FIG. 3A2 shows a clock pulse of the series of optical pulses of the time multiplexed optical signal as in FIG. 3A;

DETAILED DESCRIPTION OF THE INVENTION

The present invention relates to tissue stimulation with electrodes generally, and more specifically to stimulation of the cochlea for hearing. Although specific reference is made to cochlear implants, embodiments of the present invention can be used in many applications wherein tissue is stimulated, for example with stimulation of muscles, nerves and neural tissue, for example the treatment of Parkinson's.

As used herein light encompasses infrared light, visible light and ultraviolet light.

Figure 1A:
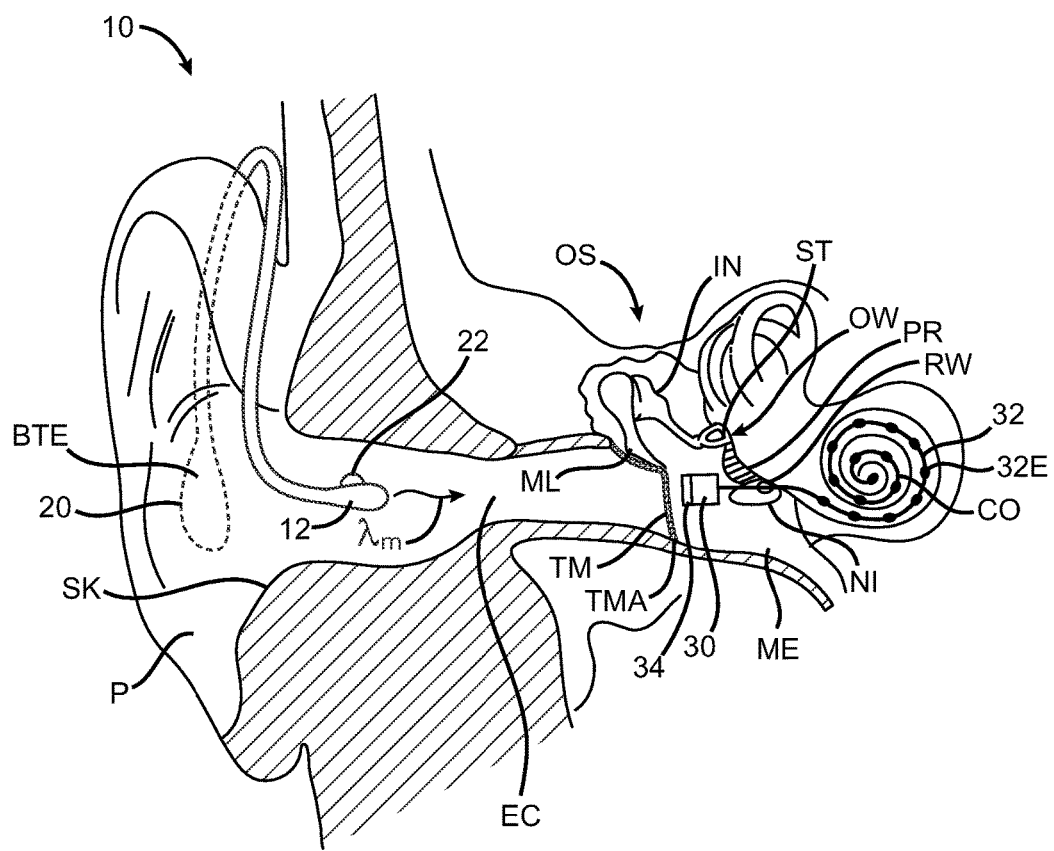
FIG. 1A shows an optically coupled cochlear implant system comprising a behind the ear unit, in accordance with embodiments of the present invention.

FIG. 1A shows an optically coupled cochlear implant system 10 comprising an input transducer assembly 20 and an output assembly 30. The input transducer assembly 20 may comprise behind the ear unit (hereinafter "BTE"). The BTE unit can be positioned behind a pinna P of the user, so as to decrease visibility of the BTE unit. The BTE unit can house electronics used to process and input signal. An input transducer, for example microphone 22, is coupled to the BTE unit and can transmit an audio signal to the BTE unit. The BTE can convert the input signal into a multiplexed optical signal $\lambda_M$. The BTE unit may house the light source which can be coupled to an optical transmission structure 12 to emit the multiplexed optical signal $\lambda_M$. The light transmission structure 12 can extend from the BTE into the ear canal EC. The light transmission structure 12 may support microphone 22. Microphone 22 can be positioned in many locations, for example within the ear canal or near the ear canal opening to detect sound localization cues. Alternatively, the microphone may be positioned on the ear canal. The input transducer may comprise a second microphone positioned on the BTE unit for noise cancelation. The sound input may comprise sound from a Bluetooth connection, and the BTE may comprise circuitry to couple with a cell phone, for example.

The output assembly 30 is configured for placement in the middle ear and inner ear of the user. The output assembly 30 comprises at least one detector 34 configured to receive the multiplexed optical signal $\lambda_M$. The output assembly comprises an electrode array 32 coupled to the at least one detector 34 so as to stimulate the cochlea in response to the multiplexed optical signal $\lambda_M$. The electrode array comprises a plurality of electrodes 32E, for example 16 pairs of electrodes. The output assembly 30 may comprise a demultiplexer coupled to the at least one detector to demultiplex the optical signal. The multiplexed optical signal may comprise, for example, a time multiplexed optical signal or a wavelength multiplexed optical signal. The demultiplexer comprises structures so as to demultiplex the optical signal and stimulate tissue of the cochlea. The demultiplexer can be configured to coupled pulses of the multiplexed optical signal with electrodes of the array such that pulses of the multiplexed optical signal correspond to electrodes of the array.

The output assembly 30 may comprise many known biocompatible and substantially non-magnetic materials, such that output assembly 30 is configured for use with MRI imaging when implanted in the patient. For example the electrode array 32 may comprise substantially non-magnetic conducting metal, such as at least one of Platinum, Titanium, Ni, or NiTinol. The electrode array may comprise a biocompatible substantially non-magnetic housing material, for example at least one of silicone elastomer, biocompatible plastic, or hydrogel.

The electrode array 32E and at least one photo detector 34 can be configured in many ways to stimulate the cochlea. For example, the electrodes can be coupled to the photo detector for monophasic pulses. The electrode array may comprise bi-phasic pulses with a first pulse corresponding to a first current in a first direction and a second pulse corresponding to a second pulse in a second direction. The light energy of the first pulse corresponding to the first direction may comprise a first amount of light energy and the second light pulse corresponding to the second direction may comprise a second amount of the light energy, and the first amount of light energy and the second amount of light energy can be substantially similar so as to decrease cumulative charging of the electrodes and/or so as to inhibit rectification and charge transfer with the electrodes, for example. The corresponding circuitry of the electrode array can be configured to transmit the audio signal and stimulate the cochlea many kinds of pulses, for example tri-phasic pulses. The light pulses of each channel may comprise a pair of pulse width modulated light pulses having a first width modulated light pulse corresponding to a first polarity of the electrode pair and a second width modulated light pulse corresponding to a second polarity of the electrode pair opposite the first light pulse. The first width modulated light pulse may have a first wavelength and the second width modulated light pulse may have a second wavelength, for example.

FIG. 1A1 shows an optically coupled cochlear implant system comprising an ear canal module (hereinafter "ECM"). The ECM may comprise many of the components of the BTE unit and vice-versa. The ECM may be shaped from a mold of the user's ear canal EC. Circuitry (CR) can be coupled to microphone 22. The circuitry may comprise a sound processor. The ECM may comprise an energy storage device PS configured to store electrical energy. The storage device may comprise many known storage devices such at least one of a battery, a rechargeable batter, a capacitor, a supercapacitor, or electrochemical double layer capacitor (EDLC). The ECM can be removed, for example for recharging or when the user sleeps. The ECM may comprise a channel 29 to pass air so as to decrease occlusion. Although air is passed through channel 29, feedback is substantially non-existent due to the electrical and non-acoustic stimulation of the cochlea.

The energy storage device PS may comprise a rechargeable energy storage device that can be recharged in many ways. For example, the energy storage device may be charged with a plug in connector coupled to a super capacitor for rapid charging. Alternatively, the energy storage device may be charged with an inductive coil or with a photodetector PV. The photodetector detector PV may be positioned on a proximal end of the ECM such that the photodetector is exposed to light entering the ear canal EC. The photodetector PV can be coupled to the energy storage device PS so as to charge the energy storage device PS. The photodetector may comprise many detectors, for example black silicone as described above. The rechargeable energy storage device can be provided merely for convenience, as the energy storage device PS may comprise batteries that the user can replace when the ECM is removed from ear canal.

The photodetector PV may comprise at least one photovoltaic material such as crystalline silicon, amorphous silicon, micromorphous silicon, black silicon, cadmium telluride, copper indium gallium selenide, and the like. In some embodiments, the photodetector PV may comprise black silicon, for example as described in U.S. Pat. Nos. 7,354,792 and 7,390,689 and available under from SiOnyx, Inc. of Beverly, Mass. The black silicon may comprise shallow junction photonics manufactured with semiconductor process that exploits atomic level alterations that occur in materials irradiated by high intensity lasers, such as a femto-second laser that exposes the target semiconductor to high intensity pulses as short as one billionth of a millionth of a second. Crystalline materials subject to these intense localized energy events may under go a transformative change, such that the atomic structure becomes instantaneously disordered and new compounds are "locked in" as the substrate re-crystallizes. When applied to silicon, the result can be a highly doped, optically opaque, shallow junction interface that is many times more sensitive to light than conventional semiconductor materials. Photovoltaic transducers for hearing devices are also described in detail in U.S. Patent Applications Nos. 61/073,271, entitled "Optical Electro-Mechanical Hearing Devices With Combined Power and Signal Architectures"; and 61/073,281, entitled "Optical Electro-Mechanical Hearing Devices with Separate Power and Signal", the full disclosures of which have been previously incorporated herein by reference and may be suitable for combination in accordance with some embodiments as described herein.

The BTE may comprise many of the components of the ECM, for example photodetector PV, energy storage device PS, the processor and circuitry, as described above.

FIG. 1A2 shows the optically coupled output transducer assembly 30 having the at least one photodetector 34 positioned in a middle ear cavity to couple optically through a posterior portion of the eardrum TM and electrode array 32E extending into the cochlea through the round window RW, as seen a medial view looking from the ear canal into the middle ear cavity through the eardrum TM. The output assembly 30 is positioned on promontory PR, for example with an attachment structure 36, such that the at least one photodetector 34 is oriented to receive light energy transmitted through a posterior portion of the eardrum TM. The position and the orientation of the at least one photodetector 34 may remain substantially fixed when light energy is transmitted through the eardrum to stimulate the cochlea with electrode array 32E. Consequently, the optical coupling, efficiency of transfer of the light energy incident on the at least photodetector 34 remains substantially constant, such that acoustic distortion due to motion of the at least one photodetector is substantially inhibited. For example, the at least one photodetector may comprise at least one photodetector PV, as described above, which is visible through the eardrum TM such that light can be transmitted from the ear canal EC through the eardrum TM so as to transmit the power and signal through the eardrum TM with light. For example, the light energy can be transmitted through a posterior portion of the eardrum, for example through a posterior/inferior portion, so as to increase coupling efficiency, for example as described herein below.

Figure 1B:
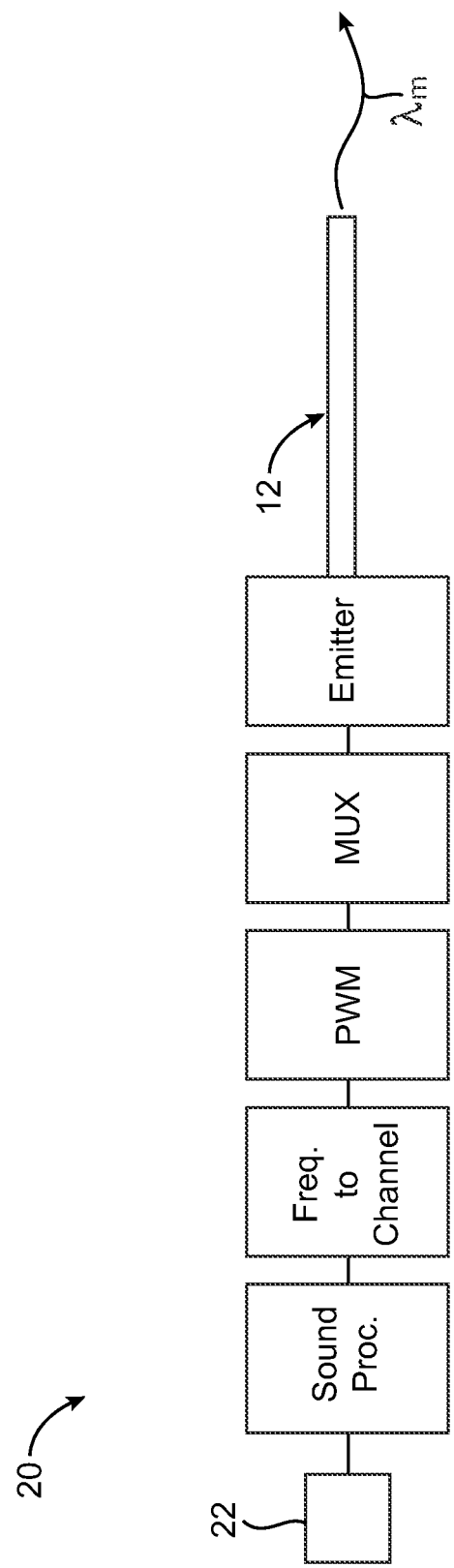
FIG. 1B shows an input transducer assembly configured to emit a multiplexed optical signal, in accordance with embodiments of the present invention.

FIG. 1B shows input transducer assembly 20 configured to emit a multiplexed optical signal. The components of the input transducer assembly may be housed in BTE unit or in the ECM, or a combination thereof. Microphone 22 is coupled to a sound processor. The sound processor may comprise one or more of many commercially available sound processors. The sound processor comprises a tangible medium to store instructions of a computer program embodied therein. The sound processor may comprise or be coupled to a multi-band frequency to channel converter. The frequency to channel converter can convert frequencies of the audio signal to filtered sound channels corresponding to locations of the cochlea for electrical stimulation such that the user perceives the sound of the audio signal. The filter for each channel may comprise a band pass filter, such that the frequencies of each channel correspond to a range of frequencies to stimulate a region along a length of the cochlea. The circuitry of in input assembly may comprise pulse width modulation (hereinafter "PWM") circuitry. The PWM circuitry can be configured to determine the width of each optical pulse corresponding to one of the electrodes of the array. The width of the optical pulse can be determined in response to the frequency of the sound corresponding to the electrode that is coupled to the optical pulse. For example, the width of the optical pulse can be determined for each of the channels with Sigma-Delta pulse width modulation, although many pulse with modulation embodiments may be used. A multiplexer MUX and an emitter can be coupled to the PWM circuitry.

The emitter comprises at least one light source. The at least one light source emits pulses of light having a duration determined by the PWM circuitry. The width of the pulse refers to the duration of the pulse. With serial multiplexing, the at least one light source may comprise a single light source, and the timing of the pulses is determined by the multiplexer. With optical multiplexing, the at least one light source comprises a plurality of light sources, for example at least three light sources. The plurality of light sources can be configured to emit light pulses substantially simultaneously. Alternatively, the plurality of light sources can be configured to emit the light pulses sequentially so as to decrease peak power consumption of the plurality of light sources.

The emitter is coupled to an optical transmission structure 12. The optical transmission structure may comprise an optical fiber, a plurality of optical fibers, a window, or an opening in the ECM. The multiplexed light is transmitted from the optical transmission structure 12 toward tissue, for example tissue of the eardrum TM, although light can be transmitted through other tissue, for example bone of openings formed in bone to transmit light.

FIG. 2A shows an input transducer assembly 20 configured to emit a wavelength multiplexed optical signal. The sound processor can determine the frequencies of the audio signal. The multi-band filtered audio signal can be converted to channels of the electrode array and corresponding wavelengths with a frequency to wavelength converter (Freq. to λ). The width of each pulse for each wavelength is determined for a plurality of wavelengths, for example at least three wavelengths. Although sixteen wavelengths are shown, many more channels can be stimulated, for example up 32. The plurality of light sources comprises a first light source configured to emit first wavelengths λ1, a second light source configured to emit second wavelengths λ2, a third light source configured to emit third wavelengths λ3 and . . . a sixteenth light source configured to emit sixteenth wavelengths λ16. Light from each source is emitted to an optical multiplexer. The optical multiplexer may comprise many known methods of optical multiplexing. For example the optical multiplexer may comprise at least one of a grating, an etalon, a prism, an optical fiber, a waveguide, a nanostructure, or a plurality of optical fibers.

The sound processor can be configured in many ways, for example as described above, and may comprise a plurality of band pass filters BPF to determine the audio signal of each channel. For example, the multi-band filtered audio signal may comprise a plurality of band pass filtered audio signals, in which each band pass filtered audio signal has a corresponding channel, such that the signal transmitted for the channel comprises a band pass filtered channel. The band pass filter for each channel may comprise one or more of a digital band pass filter or an analog band pass filter. For example, the sound processor may comprise a tangible medium having instructions of a computer program embodied thereon so as to bandpass filter the sound signal to determine the signal for each channel such that each channel comprises a digitally filtered band of frequencies corresponding to frequencies the channel. The plurality of band pass filters BPF of the input transducer assembly 20 may comprise a component of the sound processor such as a subprocessor or subroutine of the sound processor, for example. Alternatively or in combination, the plurality of bandpass filters BPF may comprise separate circuitry such as a dedicated processor.

FIG. 2A1 optical pulses comprising separate wavelengths of light of a wavelength multiplexed optical signal as in FIG. 2A. A first pulse P1 comprises first wavelengths of light and a first width W1. A Second pulse P2 comprises second wavelengths of light and a second width. A third pulse P3 comprises third wavelengths of light and a third width. A fourth pulse P4 comprises fourth wavelengths of light and a fourth width. Additional pulses, for example a total of 16 or more, can be transmitted. Although the light pulses can be transmitted simultaneously, the light pulses may be transmitted sequentially so as to decrease peak power consumption, for example as described with reference to FIG. 3A1 herein below, for example.

Each of the pulses comprise substantially separate pulses of light such that the pulses can be separated with the demultiplexer so as to correspond with one electrode of the array, or a pair of electrodes of the array. The wavelengths of each source may comprise wavelengths of a laser, in which the wavelengths of the laser correspond to the band width of the laser beam.

FIG. 2A2 shows an optical multiplexer configured to multiplex light from a plurality of light sources having separate wavelengths as in FIGS. 2A and 2A1. Light from the sources can be emitted toward an optical structure grating, for example, and combined with optical transmission structure 12. The multiplexed signal can travel along optical transmission structure 12 toward the output assembly 30. The light for each channel of the multiplexed optical signal can be emitted serially from each source, so as to decrease peak power consumption of the light sources. For example the first light source can emit a first light pulse of the packet, followed by the second light source emitting the second light source of the packet until each of the light sources corresponding to one of the channels has emitted the corresponding pulse width modulated light signal of the packet. In many embodiments, each light source emits laser light when the other light sources of the optical multiplexer do not emit light. Thus serial use of the light sources can ensure that the power storage device can provide sufficient electrical energy to each of the light sources.

Figure 2B:
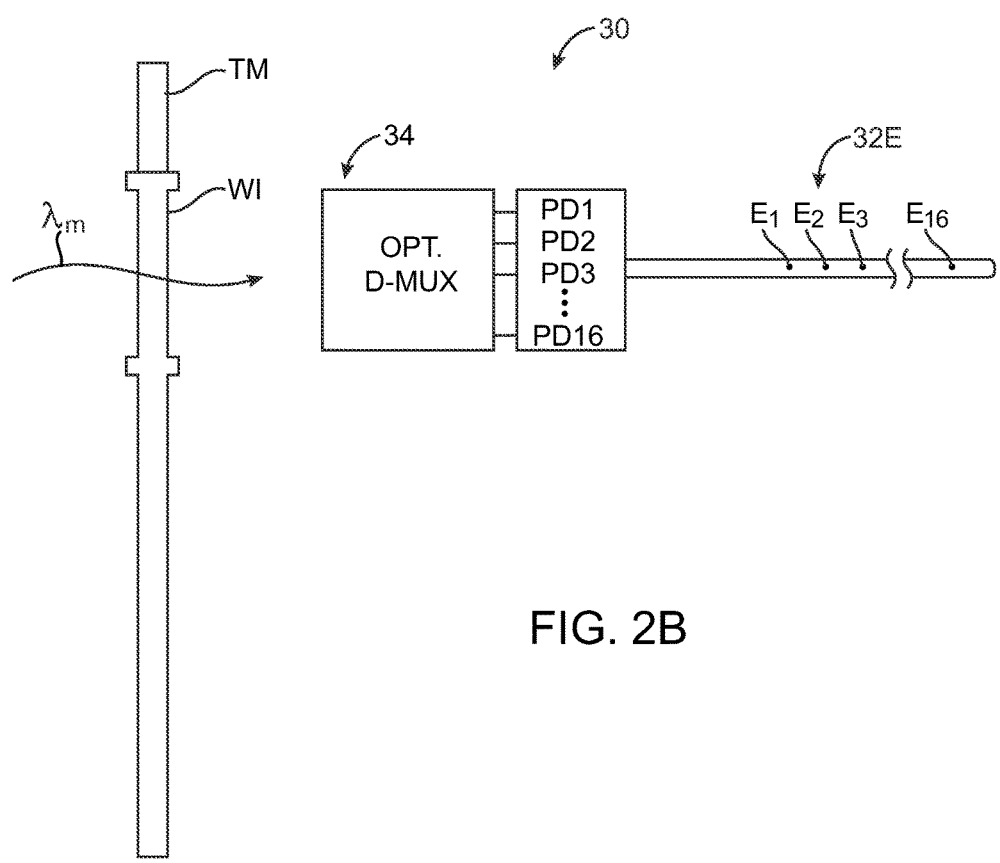
FIG. 2B shows an output transducer assembly comprising an optical demultiplexer configured to couple with an input transducer assembly as in FIG. 2A.

FIG. 2B shows an output transducer assembly configured to couple with an input transducer assembly as in FIG. 2A. The output transducer assembly comprises at least one detector 34 configured to receive the multiplexed optical signal. The at least one detector may comprise a plurality of detectors, such as a first photodetector PD1, a second photodetector PD2, a third photodetector PD3 . . . and a sixteenth photodetector PD16. Additional or fewer photodetectors may be used and may comprise many known materials as described above. An optical multiplexer can be positioned to receive the multiplexed signal beam and separate the multiplexed optical signal. The optical demultiplexer may comprise many known optical elements such as prisms, gratings, mirrors, optical fibers, waveguides, nanostructures, etc. as described above.

The multiplexed optical signal can be transmitted through tissue. For example, the multiplexed optical signal can be transmitted through an eardrum TM of the user. Alternatively or in combination, the multiplexed optical signal can be transmitted through a window WI formed in the eardrum, or an opening formed in the eardrum. The window can be helpful to maintain coherence and wavefront properties of the multiplexed optical signal. However, many embodiments do not include such structures in the eardrum.

FIG. 2C shows an output transducer assembly 30 comprising an optical demultiplexer comprising optical filters and an array of detectors. The at least one detector 34 may comprise the array of detectors. The array of detectors comprises a first detector PD1, a second detector PD2, a third detector PD3 . . . and a sixteenth detector PD16. Additional or fewer detectors can be included in the array, for example 32 detectors. The optical multiplexer may comprise optical filters positioned in front of each detector to filter light transmitted to each detector. The optical multiplexer may comprise a first optical filter F1, a second optical filter F2, a third optical filter F3 . . . and a sixteenth optical filter F16. This configuration can separate the light into channels transmitted to each detector. For example, each filter can transmit wavelengths of light that are substantially separate from the wavelengths of light transmitted by the other filters. The array of electrodes comprises a first electrode E1, a second electrode E2, a third electrode E3 . . . and a sixteenth electrode E16. Each of the electrodes may comprise a pair of electrodes, for example 16 pairs of electrodes.

Each of the detectors is coupled to a corresponding electrode of the electrode array. First detector PD1 is coupled to first electrode E1 so as to comprise a first channel. Second detector PD2 is coupled to second electrode E2 so as to comprise a second channel. Third detector PD3 is coupled to third electrode E3 so as to comprise a third channel. The output assembly may comprise additional channels. For example, sixteenth detector D16 is coupled to sixteenth electrode E16 so as to comprise a sixteenth channel. Additional or fewer channels can be provided.

The perception of loudness due to electrical stimulation of the cochlea with electrodes 32E can depend on many factors including cochlear location, pulse width (duration) and pulse height (intensity). For pulses that are 50 us, for example, the current can be as high as 200 uA for a very loud sound. For a soft sound, only a 10 uA pulse can be sufficient. Increasing the width of the pulse can decrease the required amplitude of current.

Photodetectors can be configured to generate over 1 mA of current with a 4 mm² detector. Examples include a Si detector and an InGaAs detector. Sufficient current can be generated for multiple electrodes connected to corresponding detectors based on the detector area, the pulse width, and the efficiency detector and the intensity of the light beam on the detector. Based on the teaching described herein, a person of ordinary skill in the art can determine empirically the size of the photo detectors, the intensity and duration of the light pulses to provide a full spectrum of sound from soft to loud.

The stimulation of the auditory nerve can be low pass filtered such that the rise time of each of the pulses is not critical. The encoding of each electrode may comprise one or more of many types of encoding, for example class-D amplifier encoding.

The electrode array 32E and at least one photo detector 34 can be configured in many ways to stimulate the cochlea with monophasic pulses or with bi-phasic pulses. For example, with 16 electrode pairs configured for bi-phasic pulses, the detector may comprise 16 pairs of detectors corresponding to 32 detectors. For example, each pair of electrodes can be coupled to two photodetectors, in which the two photodetectors are coupled to the electrodes with opposite polarity, such that a first light pulse to the first detector generates a first current between the electrodes in a first direction and a second light pulse to the second detector generates a second current between the two electrodes opposite the first current. The circuitry of the electrode array can be configured to delivery tri-phasic pulses, for example. The tri-phasic pulse may comprise a first current pulse of a first polarity, a second current pulse of the first polarity, and a third current pulse of a second negative polarity, in which the electrical charge delivered with the current pulse and the second current pulse approximate the charge of the third current pulse such that the total charge delivered with the three pulses is approximately balanced. The at least biphasic pulses of light can balance the amount of charge transferred so as to decrease charge accumulation of each of the pairs of the electrodes.

FIG. 2C1 shows circuitry of a channel of the output transducer assembly of FIG. 2C so as to provide at least biphasic pulses in response to a first light pulse comprising a first wavelength and a second light pulse comprising a second wavelength. The first channel C1 may comprise and/or correspond to a first pair of photodetectors comprising first photodetector PD1 and second photodetector PD1, and a first pair of electrodes comprising first electrode E1 and second electrode E2. The first photodetector PD1 can be coupled to electrode E1 and electrode E2 with a first polarity, and the second photodetector PD2 can be coupled to electrode E1 and electrode E2 with a second polarity opposite the first polarity so as to comprise a bipolar configuration of the first electrode and the second electrode. The first light pulse P1 of the first wavelength $\lambda 1$ can generate current between electrode E1 and electrode E2 in a first direction, and the second light pulse P2 of the second wavelength $\lambda 2$ can generate current between electrode E1 and electrode E2 in a second direction opposite the first direction. The width of the light pulses can be sized so as to balance charge between the electrodes and inhibit charge transfer, for example rectification. Additional channels can be provided with additional electrodes. For example, 8 channels can be provided with 8 pairs comprising 16 electrodes in a bipolar configuration, and the current can be generated in response to 16 wavelengths of light for example. Additional or fewer channels and corresponding electrodes and detectors may be provided, for example.

The photo detector array may comprise a first layer having a first array and a second layer having a second array. First wavelengths of can be absorbed by the first array, and the second wavelengths of light transmitted through the first array and absorbed by the second array, such that the combined array of the first array and second array can be decreased. Examples of detector materials having suitable properties are described in copending U.S. application Ser. No. 12/486,100 filed on Jun. 17, 2009, entitled, "Optical Electro-Mechanical Hearing Devices With Combined Power and Signal Architectures", the full disclosure of which is incorporated herein by reference.

The stacked arrangement of detector arrays can be positioned on the output transducer assembly, and can provide greater surface area for each light output signal detected. For example, the combined surface area of the detectors may be greater than a cross-sectional area of the ear canal. The first detector array may be sensitive to light comprising wavelength of about 1 um, and the second detector array can be sensitive to light comprising wavelength of about 1.5 um. The first detector array may comprise a silicon (hereinafter "Si") detector array configured to absorb substantially light having wavelengths from about 700 to about 1100 nm, and configured to transmit substantially light having wavelengths from about 1400 to about 1700 nm, for example from about 1500 to about 1600 nm. For example, the first detector array can be configured to absorb substantially light at 900 nm. The second detector array may comprise an Indium Galium Arsenide detector (hereinafter "InGaAs") configured to absorb light transmitted through the first detector and having wavelengths from about 1400 to about 1700 nm, for example from about 1500 to 1600 nm. The cross sectional area of the detector arrays can be about 4 mm squared, for example a 2 mm by 2 mm square for each detector array, such that the total detection area of 8 mm squared exceeds the cross sectional area of 4 mm squared of the detectors arrays in the middle ear cavity. The detector arrays may comprise circular detection areas, for example a 2 mm diameter circular detector area. As the middle ear cavity can be non-circular in cross-section, the detector arrays can be non-circular and rounded, for example elliptical with a size of 2 mm and 3 mm along the minor and major axes, respectively. The above detector arrays can be fabricated by many vendors, for example Hamamatsu of Japan (available on the world wide web at "hamamatsu-.com") and NEP corporation.

The light source and optical multiplexer of the input assembly can be configured in many ways to provide bandwidths suitable for use with two overlapping detector arrays. The light source and multiplexer can be combined with known wavelength multiplexing systems suited for incorporation in accordance with embodiments as described herein, such as components the EPIC integrated channelizer of the MIT Microphotonics Center and the photonics components available from Intel. The light source may comprise an integrated optical RF channelizer on silicon comprising an integrated photonics chip and laser light source. A first light laser source can be configured to emit light having wavelengths suitable for absorption with the first array, and the first light source can be coupled with a first modulator to modulate the first light beam so as to correspond to channels of the first array detector. A second light laser source can be configured to emit light having wavelengths suitable for transmission through the first array and absorption with the second array, and the second light source can be coupled with a second modulator to modulate the light beam so as to correspond to channels of the first array detector. The modulated light signals can be received by a multimode interferometeric splitter to demultiplex the transmitted light signal, for example. Transmission through an optical window or opening of the eardrum can retain integrity of the transmitted light.

Figure 3A:
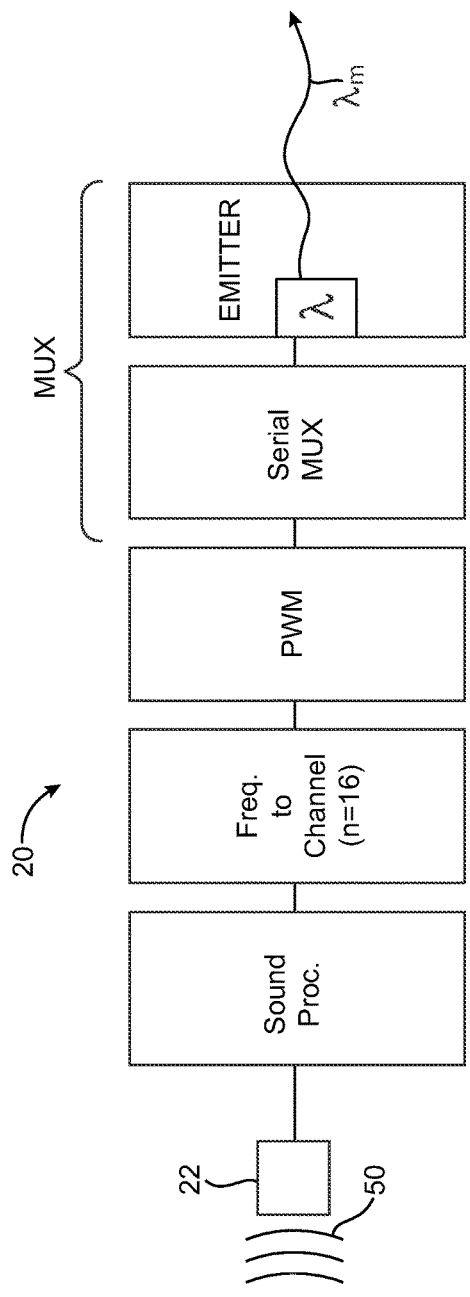
FIG. 3A shows an input transducer assembly configured to emit a time multiplexed optical signal in accordance with embodiments of the present invention.
Figure 3A:
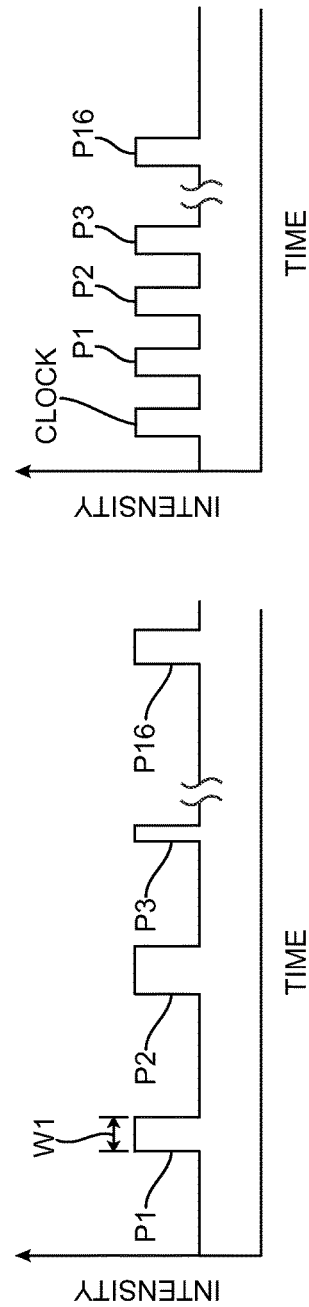

FIG. 3A shows an input transducer assembly configured to emit a time multiplexed optical signal. The multiplexed optical signal $\lambda_M$ may comprise the time multiplexed optical signal, for example a serial multiplexed optical signal. An audio signal 50, for example a sound, is received by microphone 22. The audio signal comprises an input to the sound processor. The frequencies of the audio signal can be determined, for example with circuitry as described above. The frequencies of the audio signal can be used to determine the amount of stimulation for each electrode of the array, in which each electrode corresponds to a channel. The width of each optical pulse can be determined with the PWM circuitry. The PWM circuitry is coupled to a serial multiplexer to multiplex the pulses for each electrode. The serial multiplexed pulses are emitted from an emitter comprising the at least one light source. The at least one light source may comprise a single light source, such as an infrared laser diode.

FIG. 3A1 optical pulses comprising a series of pulses of the time multiplexed optical signal as in FIG. 3A. The multiplexed serial pulses comprise a first pulse P1, a first pulse P1, a second pulse P2, a third pulse P3 . . . and a sixteenth pulse P16. Each pulse corresponds to one electrode of the array. An amount of electrical current is determined by a width of the pulse. First pulse P1 comprises a first width W1. Second pulse P2 comprises a second width. Third pulse P3 comprises a third width. Sixteenth pulse P16 comprises a sixteenth width. The multiplexer can be configured to emit packets of pulses, in which each packet comprises pulse information for each electrode of the array. For example, a packet may comprise sixteen pulses for the sixteen electrodes of the array. The serial multiplexer can be configured to emit the pulses of each packet so as to correspond with a predetermined timing and sequence of the pulses.

FIG. 3A2 shows a clock pulse of the series of optical pulses of the time multiplexed optical signal as in FIG. 3A. The clock pulse can synchronize the packet with the demultiplexer, such that the pulses are demultiplexed so as to correspond with the appropriate electrode. For example, pulse P1 may correspond with electrode E1. The clock pulse provide power to the demultiplexer circuitry.

Figure 3B:
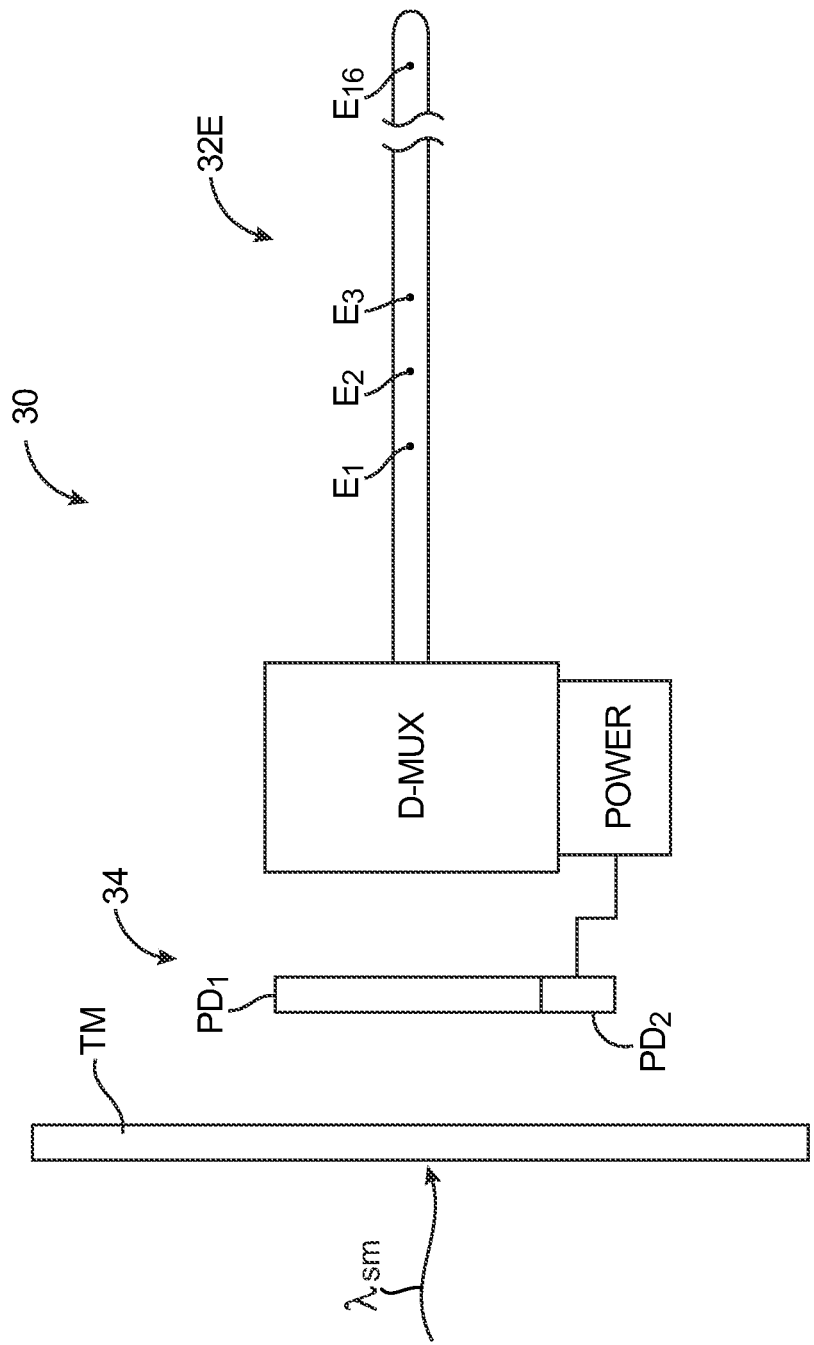
FIG. 3B shows an output transducer assembly configured for use with an input transducer assembly as in FIG. 3A.

FIG. 3B shows an output transducer assembly configured for use with an input transducer assembly as in FIG. 3A. The serial multiplexed optical signal is transmitted through the eardrum TM. The multiplexed optical signal is received by a photo detector PD1. Photodetector PD1 is coupled to demultiplexer circuitry D-MUX. The circuitry D-MUX may comprise a timer and switches such that the multiplexer sequentially couples each electrode to the detector in accordance with a predetermined sequence such that the detector is coupled to one of the electrodes when the pulse corresponding to the electrode is incident on detector PD1. For example, the pulse sequence may comprise a packet of pulses as described above. The first pulse of the packet may comprise a clock pulse to power the circuitry and to reset the timer. The timer can be coupled to the switches of the multiplexer such that a switch corresponding to one electrode is closed when the optical pulse corresponding to the electrode arrives at the detector. The timer and switches may comprise low power circuitry, for example CMOS circuitry, such that the timer and switches can be powered with the clock pulse. This can be helpful when the audio signal is weak such that the timer and switching circuitry has sufficient power. Power storage circuitry such as capacitors and super capacitors can be coupled to the detector PD1 to store energy from the clock pulse with power circuitry (Power). The power circuitry can be switched with the switching circuitry such that the power storage capacitors are decoupled from the detector PD1 when the light pulses for the electrodes arrive at detector PD1.

The serial light source and detector components may comprise silicon photonics components of the MIT Microphotonics Center and the photonics components commercially available from Intel, as described above.

In some embodiments, the power circuitry can be coupled to a separate detector PD2. The separate power and signal can be used to power the timing and switching circuitry.

Figure 4:
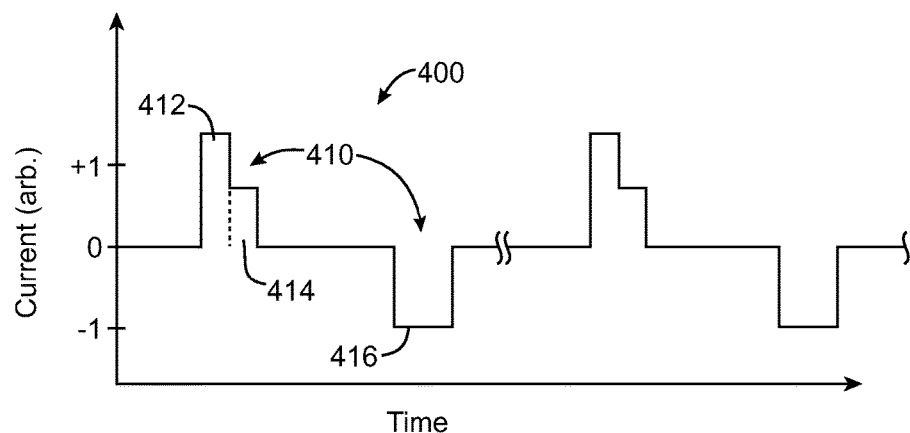
FIG. 4 shows tri-phasic pulse width modulated pulses, in accordance with embodiments.

FIG. 4 shows tri-phasic pulse width modulated current pulses 400 corresponding to a channel of the electrode array. Each of the channels may comprise a pair of electrodes and the current pulses can be transmitted between the pair of electrodes corresponding to the channel. The tri-phasic current pulses 400 may comprise a first positive current pulse 412, a second positive current pulse 414 and a third negative current pulse 416. The first positive current pulse 412 and the second positive current pulse 410 comprise a positive amplitude to inject current may comprise a first amplitude and a second amplitude. Alternatively or in combination, the first positive current pulse 412 and the second positive current pulse 414 may comprise a substantially similar amplitude substantially different widths. The third negative current pulse comprises a negative polarity to balance the current and decrease degradation of the electrodes and tissue near the electrodes. The first positive current pulse and the second positive current pulse may transfer a first amount of charge and a second amount of charge with the current, respectively, and the third negative current pulse may transfer a third amount of current so as to balance the charge of the first pulses and decrease charge build up of the electrodes. As the area under a current pulse corresponds to the delivered charge of the current pulse, the cumulative area of the first positive current pulse and second positive current pulse may correspond substantially to the area of the cumulative area of the third negative pulse.

The photodetectors and filters can be coupled to the electrodes so as to pass at least biphasic current between the electrodes. Each of the plurality of channels may correspond to a pair of electrodes, and a first current can travel between said pair of electrodes in response to a first width modulated light pulse corresponding to positive current pulse 412 and a second current corresponding to negative pulse 416 may travel between said pair of electrodes in response to a second width modulated light pulse, as described above with reference to FIG. 2C and FIG. 2C1, for example. The first width modulated light pulse corresponding to positive pulse 412 may comprise a first wavelength of light and the second width modulated light pulse corresponding to negative pulse 416 may comprise a second wavelength of light. The second current pulse 414 may correspond to a second light pulse having the first wavelength, for example. The first current is opposite the second current. The first current has a first amount corresponding to a first width of the first light pulse and the second current has a second amount corresponding to a second width of the second light pulse. The width of the first light pulse corresponds substantially to the width of the second light pulse so as to inhibit rectification and balance charge transfer between the first electrode and the second electrode.

The first light pulse may comprise a first wavelength of light coupled to a first detector, in which the second detector is coupled to said pair of electrodes. The second light pulse may comprise a second wavelength of light coupled to a second detector, in which said second detector is coupled to said pair of electrodes. The first detector is coupled to said pair of electrodes opposite the second detector. Each channel may correspond to a pair of electrodes and a first detector coupled to the pair of electrodes opposite a second detector, for example at least about 8 channels corresponding to 8 pairs of electrodes coupled 16 detectors.

Figure 5B:
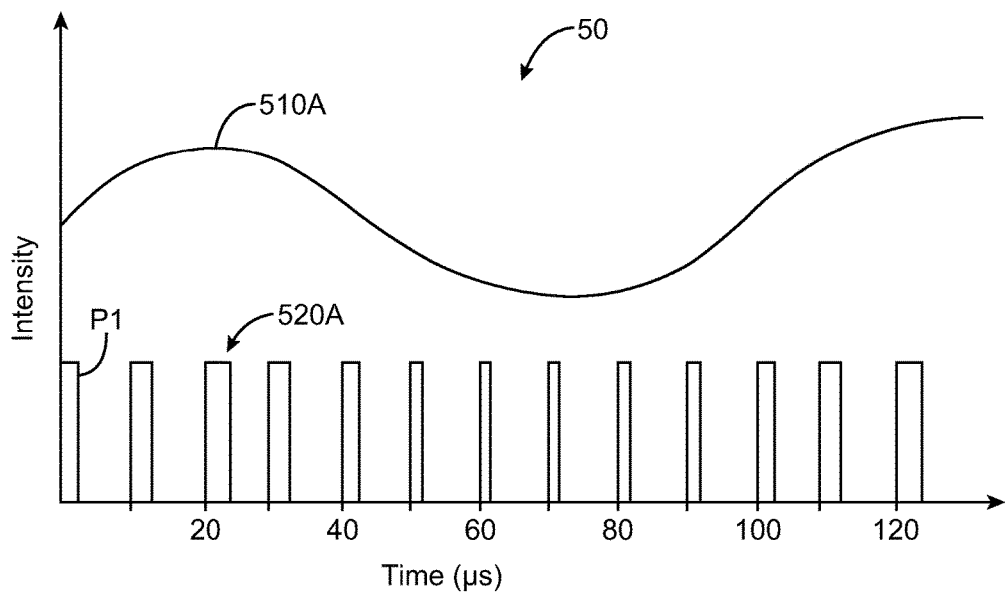
FIG. 5B shows pulses of a channel for high frequency stimulation of the cochlea so as to maintain phase of the audio signal as in FIG. 5A.
Figure 5A:
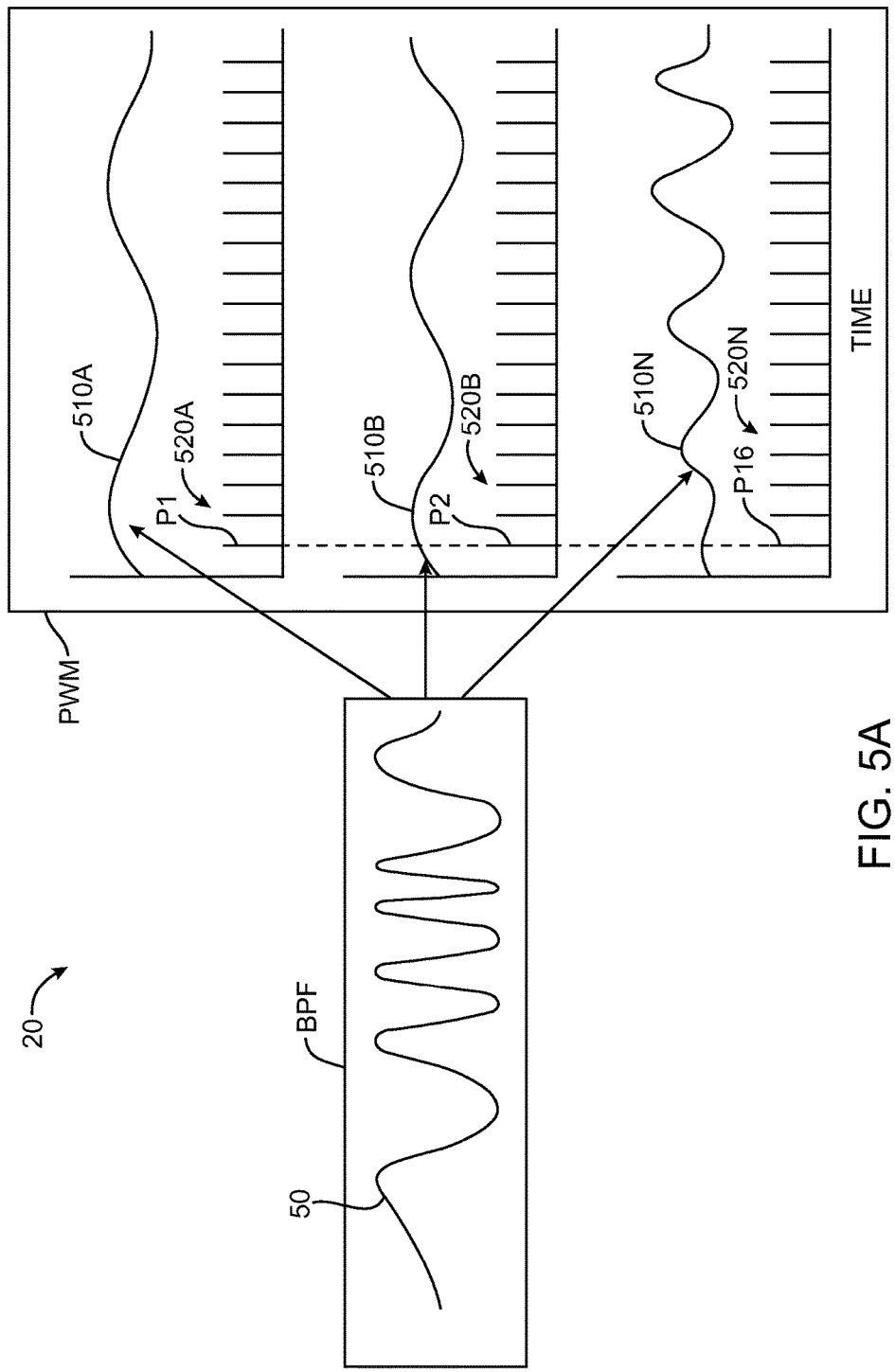
FIG. 5A shows signal to channel conversion with bandpass filtering and pulse width modulation so as to maintain substantially phase of the audio signal among the channels with high frequency stimulation of the cochlea, in accordance with embodiments.

FIG. 5A shows signal to channel conversion with bandpass filtering and pulse width modulation so as to maintain substantially phase of the audio signal among the channels with high frequency stimulation of the cochlea. Work in relation to embodiments as described herein indicates that the cochlea can respond to high frequency electrical stimulation so as to low pass filter the high frequency stimulation, such that the person can perceive sound based on the electrical stimulation, for example electrical stimulation having frequencies above the range of hearing of the patient. For example, with stimulation of high frequencies above about 10 kHz, for example above about 20 kHz, the cochlea can low pass filter the sound such that the patient hears the sound with phase of the audio signal. When these high frequencies comprise phase encoded information of the audio signal, the user can hear the audio signal with the corresponding phase. The high frequency signal above about 10 kHz, for example above 20 kHz, such as 40 kHz or 100 kHz, may comprise a pulse width modulated signal with amplitude and phase encoding with high frequencies, and the stimulation of the cochlea with the width modulated pulses at these high frequencies can result in demodulation of the high frequency pulse width modulated signal back into an audio band signal corresponding to the frequencies of the bandpass filtered channel. This demodulation of the high frequency amplitude and phase encoded signal can maintain both the amplitude and phase of the audio signal perceived by the user.

The audio signal 50 corresponding to a sound may comprise many frequencies and can be input into a bandpass filter BPF. The bandpass filter BPF may provide as output a first 2 channel comprising first band pass audio signal 510A comprising a first range of frequencies, a second channel comprising a second band pass audio signal 510B comprising a second range of frequencies, and an Nth channel comprising an Nth band pass audio signal 510A comprising an Nth range of frequencies. Each of the signals may comprise a substantially similar phase such that the phase of the BPF output is substantially maintained.

The audiosignal of each channel is converted to a pulse with modulated signal such that the phase of the original audio signal 50 is maintained among the channels. First bandpass audiosignal 510A corresponds to a first series 520A of width modulated pulses. Second bandpass audiosignal 510B corresponds to a second series 520B of width modulated pulses. Nth bandpass audiosignal 510N corresponds to an Nth series 520N of width modulated pulses. Each of the pulses may be determine so as to correspond to a substantially synchronous time base, such that each of the phase and amplitude of the original signal is maintained. For example, each of the pulses may be output to a corresponding light source to drive a corresponding photodetector, as described above. The Nth channel may comprise an eight channel, a sixteenth channel, a thirty second channel or a sixty fourth channel for example.

FIG. 5B shows a first series of width modulate pulses 520A of the first bandpass audiosignal 510A of the first channel for high frequency stimulation of the cochlea so as to maintain phase of the audio signal as in FIG. 5A. The pulses may correspond to a synchronous a time base of 10 us between the leading edge of each pulse. The width of the pulses can vary based on the amplitude of the first bandpass filtered audio signal 510A. The corresponding frequency of the pulses is about 100 kHz and the pulses are demodulated by the cochlea with cochlear low pass filtering such that the user perceives sound with phase of the sound maintained and such that the user can perceive sound localization cues.

The bandpass filtered signals of the other channels can be processed similarly with cochlear low pass filtering of the high frequency signal such that the user perceives sound with phase of the sound maintained for each of the channels and such that the user can perceive sound localization cues from the combined channels.

While the pulse width modulated light pulses can be generated in many ways, the speech processor may comprise digital bandpass filters to output the bandpass filtered signal as an array for each channel, and the pulse width modulation circuitry can determine a width of each pulse of each channel based on the output, for example. As the output of the pulse width modulation circuitry can be digital and stored in the random access memory of the processor, the pulses to the light source can be delivered so as to maintain substantially the amplitude and phase of the output pulse modulation signal. For example, the timing and/or phase of the pulses of the signal can be maintained to within about 100 us for a 10 kHz pulse width modulation signal, and within about 10 us for a 100 kHz. Although the serial output among the channels may be used as described above and the timing and/or phase of each of the pulses of the channels may be shifted slightly relative to each other, the timing and/or phase of the corresponding pulses among the channels is substantially maintained with the serial output. For example, the corresponding light pulses of the serial output among the channels can be maintained to within about 100 us, for example within about 50 us, within about 20 us, or within about 10 us. The number of channels may comprise 2 channels, 4 channels, 8 channels, 16 channels, 32 channels or more for example. The frequency of the light pulses of each channel can be above at least about 10 kHz, for example 20 kHz, 40 kHz, 80 kHz, for example. The channels may be combined having the frequency of the light pulses of each channel as described above, such that the frequency of the width modulated pulses of the multiplexed optical signal transmitted across the eardrum may comprise, 40 kHz, 160 kHz, 640 kHz, 1280 kHz, or more, for example. Based on the teachings described herein, a person of ordinary skill in the art can determine the number of channels and the timing and/or phase of the pulses to maintain the phase of the audio signal when the cochlea is stimulated, for example so as to provide sound localization cues and so as to inhibit distortion.

Human Eardrum Transmission Experiment

The below described experiment was conducted to measure transmission of infrared light through the eardrum and determine arrangements of the input assembly 20 and output assembly 30.

Objective: To determine the amount of light transmission loss through a human eardrum at posterior, inferior and anterior positions and the amount of scatter by the eardrum.

Figure 6:
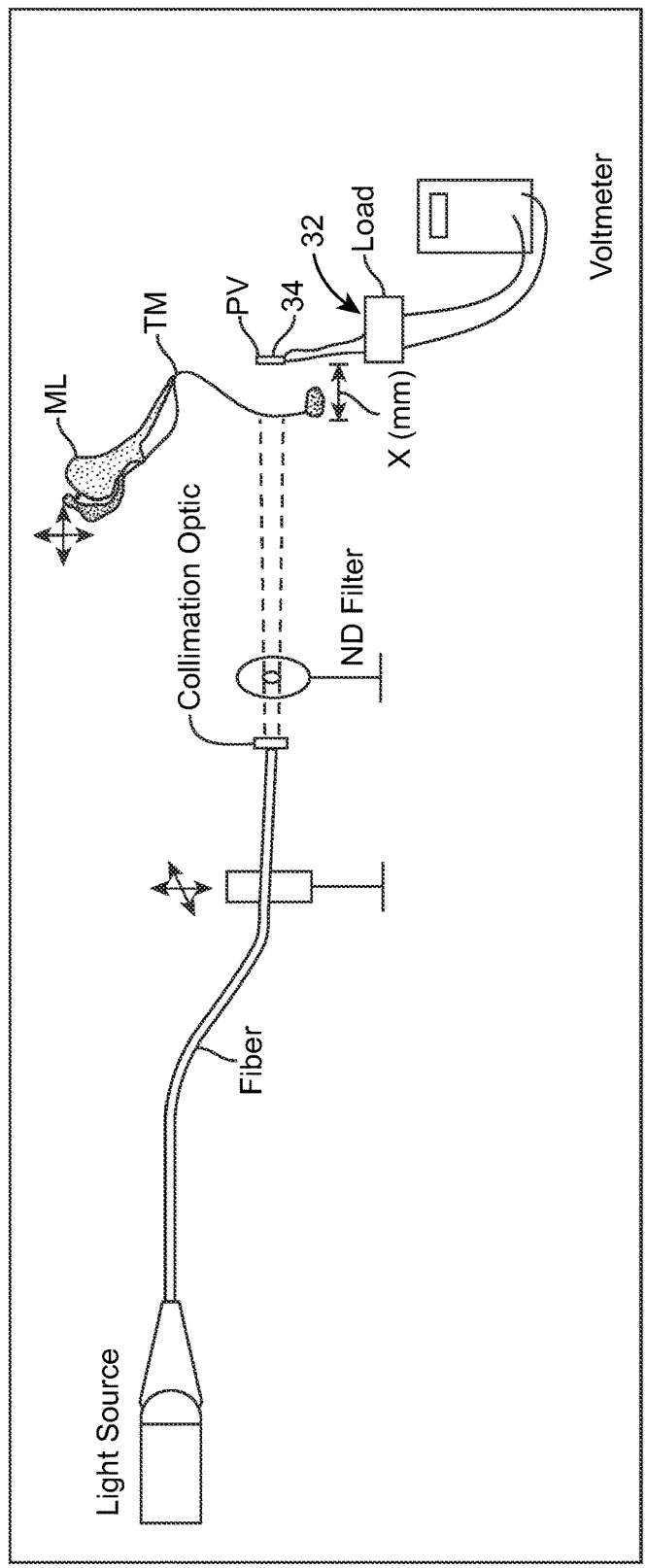
FIG. 6 shows an experimental set up to determine optical transmission through the tympanic membrane, in accordance with embodiments.

Procedure:

FIG. 6 shows the experimental set up to determine optical transmission through the tympanic membrane, in accordance with embodiments. A fiber optic coupled laser diode light source was aligned with a photodiode optical detector. An eardrum was placed in line and the change in optical output from the photodiode determined. The eardrum is mounted to a x, y, z translation stage which allows a change to different positions of the eardrum that the light goes through.

Materials:

Light source—1480 nm laser diode coupled to an optical fiber (250 um diameter, 80 um core);

PhotoDiode—1480 nm photodiode (5.5 mm2);

Load—RLC electrical circuit equivalent to that of a balanced armature transducer coupled to a diaphragm, which can be suitable for determining transmission through the eardrum.

Collimation optics and a Neutral Density Filter (NE20B);

DC Voltmeter (Fluke 8060A);

Translation stages; and

Human cadaver eardrum with attached malleus (incus and other medial components removed)

Results

No Tympanic Membrane

The current was set such that the photodiode was in the saturation region. A neutral density (ND) filter was used to attenuate the light output to reduced the PD response. The measurements indicate that the ND filter attenuated the light source by 20.5 dB. This ensured that all measurements reported are from the linear region.

The photodiode voltage in response to the collimated light beam without the eardrum was measured at the beginning of the measurements and at the end of experiment. The difference was less than 1%.

With no TM and ND filter, the output in mV was 349. With the ND filer and no TM, this output decreased to within a range from about 32.9 to 33.1, corresponding to a linear change of 0.095 and −20.5 dB.

With Tympanic Membrane

Measurements were made at anterior, inferior, and posterior positions of the eardrum. The eardrum was moved at different locations relative to the photodiode and it's distance X (in mm) approximated. Table 1 shows the measured voltages corresponding to the different positions and different eardrum locations.

TABLE 1

Measured photodiode voltages corresponding to transmission loss from the eardrum

| x (mm) | 0.1 | 0.5 | 1 | 2 | 3 |
|---|---|---|---|---|---|
| Posterior | 28 mV | 26.6 mV | 25.4 mV | 23.4 mV | 20.6 mV |
| Inferior | | | 23.6 mV | 21.1 mV | 17.1 mV |
| Anterior | | | 21.4 mV | 20.2 mV | 18.2 mV |

The posterior placement shows the highest voltage for all distances and has values of 28, 26.6, 25.4 23.4 and 20.6 for distances of 0.1, 0.5, 1, 2 and 3 mm, respectively.

For each eardrum position and location, the optical fiber was adjusted to maximize the PD voltage. This ensured that the light beam was maximally on the photodiode surface and that the measured response was due to transmission loss and not due to misalignments.

Calculations

The measured voltages were converted to percent transmission loss (hereinafter "TL") as follows:

$$\%TL = ((V_{NoTM} - V_{WithTM})/V_{NoTM}) * 100$$

where $V_{NoTM}$ is the measured voltage with no tympanic membrane and $V_{withTM}$ is the measured voltage with the tympanic membrane Table 2 below shows the calculated % Transmission Loss using the above equation.

TABLE 2

| | % Transmission loss | | | | |
|---|---|---|---|---|---|
| x (mm) | 0.1 | 0.5 | 1 | 2 | 3 |
| Posterior | 16 | 20 | 23 | 29 | 38 |
| Inferior | | | 29 | 36 | 48 |
| Anterior | | | 35 | 39 | 45 |
| Average | | | 29 | 35 | 44 |

At all locations the posterior placement showed the least transmission loss and values of 16, 20, 23, 29 and 38% at distances of 0.1, 0.5, 1, 2 and 3 mm, respectively.

With the PD very close to the eardrum (within about 0.1 mm), the TL is about 16%. The TL could only be measured for the Posterior position.

Of the three positions of the eardrum, the posterior position is better than the inferior position by 6-10%, and better than the anterior position by 7-12%.

As the eardrum is moved away from the PD, the transmission loss increases linearly for all three positions. The average transmission loss is about 29%, 35%, and 44% averaged across the three different positions for the 1, 2 and 3 mm locations respectively.

Experimental Conclusions

The transmission loss due to the eardrum is lowest at the posterior position (16%). The loss increases as the photodiode is moved away from the eardrum due to scatter of the collimated beam by the eardrum. At 3 mm from the eardrum, the average loss was as much as 44%. These data shown the unexpected result that there is more loss due to light scatter at angles away from the detector surface induced by the eardrum than due to transmission of light through the eardrum, and the detector and coupler such as a lens can be shaped appropriately so as to collect transmitted light scattered by the eardrum. These data also show the unexpected result that light transmission is higher through the posterior portion of the eardrum.

As the eardrum can move, the detector in a living person should be at least about 0.5 mm from the eardrum. The data suggest that a detector and/or component such as a lens can be shaped to fit the eardrum and provide improved transmission, for example shape with one or more of an inclined surface, a curved surface, and can be positioned within a range from about 0.5 mm to about 2 mm, for example.

The above data shows that illuminating a portion of the eardrum and placing a detector near the illuminated portion, for example can achieve transmission coupling efficiency between the projected light beam and detector of a least about 50% (corresponding to 50% loss), for example at least about 60% (corresponding to 40% loss). With posterior placement of the detector and illumination of a portion of the posterior region of the eardrum, the coupling efficiency can be at least about 70%, for example 80% or more. These unexpectedly high results for coupling efficiency indicate that illumination of a portion of the eardrum and a detector sized to the illuminated portion can provide efficiencies of at least about 50%. Also, the unexpected substantially lower transmission loss for the posterior portion of the eardrum as compared to each of the inferior and anterior portions indicates that transmission can be unexpectedly improved with posterior placement when most of the eardrum is illuminated. For example, the transmission coupling efficiency of the optical fiber to the photodetector can be improved substantially when the photodetector is positioned in the posterior portion of the middle ear cavity, for example the inferior posterior portion of the middle ear cavity, and an optical fiber is positioned in the ear canal without collimation optics such that light is emitted directly into the ear canal from the end of the optical fiber. Also, the high amount of light transmission through the eardrum shows that the optically multiplexed light can be transmitted through the eardrum, and that the channels of sound encoded with the optically multiplexed signal transmitted through the eardrum can stimulate channels of the cochlea.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims and the full scope of the equivalents thereof.

What is claimed is:

1. A system to stimulate tissue of a user having a tympanic membrane, the system comprising:
    a plurality of electrodes configured for placement at least partially within the tissue;
    circuitry configured to receive a signal from a source;
    at least one light source coupled to the circuitry, the at least one light source and the circuitry configured to transmit through the tympanic membrane a multiplexed optical signal comprising a plurality of light pulses;
    at least one photodetector sized and shaped to collect a scattered multiplexed optical signal transmitted through the tympanic membrane, the at least one photodetector and the plurality of electrodes configured to pass current through the electrodes in response to the scattered multiplexed optical signal comprising the plurality of light pulses in order to stimulate the tissue,
    wherein the multiplexed optical signal comprises a plurality of optical channels, each optical channel of the plurality corresponding to at least one frequency of sound, and
    wherein the multiplexed optical signal is transmitted through the tympanic membrane of the user to the at least one photodetector, the at least one photodetector configured to be affixed to a middle ear and coupled to the plurality of electrodes configured to be positioned at least partially within a cochlea.

2. The system of claim 1, wherein the multiplexed optical signal comprises an audio signal to be transmitted to the user.

3. The system of claim 1, wherein the tympanic membrane acts as a transmission medium for the transmitted multiplexed optical signal.

4. The system of claim 1, wherein the multiplexed optical signal is configured to provide power to the plurality of electrodes in order to stimulate the tissue.

5. A system to transmit an audio signal to a user having a tympanic membrane, the system comprising:
    an electrode array comprising a plurality of electrodes configured for placement at least partially within a cochlea of the user;
    circuitry configured to receive the audio signal from a sound source;
    at least one light source coupled to the circuitry, the at least one light source and the circuitry configured to transmit through the tympanic membrane a multiplexed optical signal comprising a plurality of light pulses and comprising the audio signal, wherein the multiplexed optical signal comprises a plurality of optical channels, each optical channel of the plurality corresponding to at least one frequency of the audio signal;
    at least one detector sized and shaped to collect a scattered multiplexed optical signal transmitted through the tympanic membrane and pass current through the electrodes in response to the scattered multiplexed optical signal comprising the plurality of light pulses in order to transmit the audio signal,
    wherein the multiplexed optical signal is transmitted through the tympanic membrane of the user to the at least one detector, the at least one detector configured to be affixed to a middle ear and coupled to the electrode array configured to be positioned at least partially within a cochlea.

6. The system of claim 5 wherein the circuitry is configured to determine widths of a plurality of light pulses and wherein each light pulse corresponds to an electrode of the array and a width of said each light pulse corresponds to an amount of current through said corresponding electrode of the array.

7. The system of claim 5 wherein the circuitry is configured to determine frequencies of the audio signal and wherein the frequencies correspond to electrodes of the array and wherein the circuitry is configured to determine a width of each pulse in response to one or more of the frequencies.

8. The system of claim 5 wherein the at least one light source comprises a plurality of light sources and wherein each light source corresponds to one electrode of the array.

9. The system of claim 8 each of the plurality of light sources is configured to emit light comprising wavelengths separated from wavelengths of other light sources of the plurality.

10. The system of claim 8 wherein the plurality of light sources comprises at least three light sources and the electrode array comprises at least three electrodes and wherein each of the at least three light sources corresponds to one electrode of the at least three electrodes of the array.

11. The system of claim 10 each of the at least three light sources is configured to emit light comprising wavelengths separated from others of the at least three light sources and wherein the wavelengths of each source correspond to one electrode of the at least three.

12. The system of claim 5 wherein the at least one detector comprises a plurality of detectors and wherein each detector of the plurality corresponds to one electrode of the array.

13. The system of claim 12 wherein the plurality of light detectors comprises at least three light detectors and the electrode array comprises at least three electrodes and wherein each of the at least three light detectors corresponds to one electrode of the at least three electrodes of the array.

14. The system of claim 5 further comprising an optical structure configured to receive the scattered multiplexed optical signal, the optical structure configured for placement in a middle ear of the user, the optical structure configured to select wavelengths of the scattered multiplexed optical signal.

15. The system of claim 14 wherein the said optical structure is sized to pass through an incision in the tympanic membrane for placement in the middle ear and wherein the electrode array is sized for placement at least partially inside the cochlea through a round window of the cochlea.

16. The system of claim 14 wherein the optical structure comprises at least one of an optical filter, a grating, an etalon, a plurality of optical fibers, or a prism.

17. The system of claim 14 wherein the plurality of optical channels corresponds to at least sixteen channels and said at least one frequency corresponds to at least sixteen frequencies.

18. The system of claim 14 further comprising an elongate optical transmission structure configured for placement at least partially within an ear canal of the user and wherein the elongate optical transmission structure is configured to transmit multiplexed optical signal through the tympanic membrane.

19. The system of claim 5 wherein the at least one photodetector and the electrode array are sized to pass through an incision in the tympanic membrane.

20. The system of claim 5 wherein the multiplexed optical signal comprises a wavelength multiplexed optical signal, the wavelength multiplexed optical signal comprising a plurality of wavelengths such that each wavelength corresponds to an electrode of the array.

21. The system of claim 20 wherein each wavelength of the plurality corresponds to an electrode of the array.

22. The system of claim 20 wherein the plurality of wavelengths comprises at least three wavelengths and wherein the plurality of electrodes comprises at least three electrodes and wherein each wavelength of the plurality corresponds to one electrode of the at least three electrodes.

23. The system of claim 5 wherein the circuitry is configured to transmit a series of the light pulses corresponding to electrodes of the array.

24. The system of claim 23 wherein the series of light pulses comprises a plurality of light pulses and wherein each light pulse of the plurality corresponds to one electrode of the plurality.

25. The system of claim 24 wherein the plurality of electrodes comprises at least three electrodes and wherein the series comprises at least three light pulses and wherein each light pulse of the at least three light pulses corresponds to one electrode of the at least three electrodes.

26. The system of claim 23 wherein the series comprises a timing light pulse.

27. The system of claim 26 wherein the timing light pulse comprises a substantially fixed width and wherein the timing light pulse comprises energy to power circuitry coupled to the plurality of electrodes.

28. The system of claim 26 further comprising switching circuitry coupled to the at least one detector to couple sequentially each electrode of the plurality to the at least one detector in response to the timing pulse such that each pulse of the series corresponds to one electrode of the plurality.

29. The system of claim 28 wherein the series of pulses comprises a predetermined order and timing of the pulses and wherein the switching circuitry comprises a timer coupled to switches to open the switches and close the to correspond with pulses of the series.

30. The system of claim 28 wherein the series comprises at least three pulses and wherein the switching circuitry is configured to coupled at least one detector sequentially to each electrode of the at least three such that each pulse of the series corresponds to one electrode of the plurality.

31. The system of claim 5 wherein the electrode array and the at least one detector comprise non-magnetic materials configured for MRI imaging when implanted in the user.

32. The system of claim 5 wherein the sound comprises a phase and wherein the optical signal comprises width modulated light pulses transmitted with a frequency of at least about 10 kHz and wherein each light pulse generates an electrical current within the cochlea such that the cochlea demodulates the light pulses and the phase of the sound is maintained.

33. The system of claim 32 wherein the width modulated light pulses comprises a series of width modulated pulses for each channel and wherein the series of width modulated pulses of said each channel comprises a frequency of at least 10 kHz to maintain the phase of the sound when the user hears the sound.

34. The system of claim 33 wherein the frequency of said each series comprises at least 20 kHz to maintain the phase of the sound when the user hears the sound.

35. The system of claim 34 wherein the plurality of channels comprises at least eight channels and the frequency of the width modulated light pulses comprises at least 160 kHz.

36. The system of claim 33 wherein the light pulses of the series of width modulated pulses of each channel are combined to form a sequence of packet of pulses, each packet comprising one pulse from each series.

37. The system of claim 36 wherein each of the plurality of channels corresponds to a pair of electrodes and wherein a first current travels between said pair of electrodes in response to a first width modulated light pulse and a second current travels between said pair of electrodes in response to a second width modulated light pulse, the first current opposite the second current, the first current opposite the second current, the first current having a first amount corresponding to a first width of the first pulse and the second current having a second amount corresponding to a second width the second pulse, and wherein the width of the first pulse corresponds to the width of the second pulse so as to inhibit rectification and balance charge transfer between the first electrode and the second electrode.

38. The system of claim 37 wherein the first light pulse comprises a first wavelength of light coupled to a first detector coupled to said pair of electrodes and wherein the second light pulse comprises a second wavelength of light coupled to a second detector coupled to said pair of electrodes and wherein the first detector is coupled to the pair opposite the second detector.

39. The system of claim 5, wherein the tympanic membrane acts as a transmission medium for the transmitted multiplexed optical signal.

40. The system of claim 5, wherein the multiplexed optical signal is configured to provide power to the plurality of electrodes in order to stimulate tissue of the user.

\* \* \* \* \*